(12) United States Patent
Zhou et al.

(10) Patent No.: US 12,427,173 B2
(45) Date of Patent: Sep. 30, 2025

(54) USE OF BACTERIA, BACTERIAL PRODUCTS, AND OTHER IMMUNOREGULATORY ENTITIES IN COMBINATION WITH ANTI-CTLA-4 AND/OR ANTI-PD-1 ANTIBODIES TO TREAT SOLID TUMOR MALIGNANCIES

(71) Applicants: THE JOHNS HOPKINS UNIVERSITY, Baltimore, MD (US); BIOMED VALLEY DISCOVERIES, INC., Kansas City, MO (US)

(72) Inventors: Shibin Zhou, Owings Mills, MD (US); Bert Vogelstein, Baltimore, MD (US); Kenneth Kinzler, Baltimore, MD (US); Kibem Kim, Lutherville, MD (US); Saurabh Saha, Wellesley Hills, MA (US)

(73) Assignee: Biomed Valley Discoveries, Inc., Kansas City, MO (US)

( * ) Notice: Subject to any disclaimer, the term of this patent is extended or adjusted under 35 U.S.C. 154(b) by 267 days.

(21) Appl. No.: 15/301,163

(22) PCT Filed: Mar. 31, 2015

(86) PCT No.: PCT/US2015/023633
§ 371 (c)(1),
(2) Date: Sep. 30, 2016

(87) PCT Pub. No.: WO2015/153639
PCT Pub. Date: Oct. 8, 2015

(65) Prior Publication Data
US 2017/0020931 A1    Jan. 26, 2017

Related U.S. Application Data

(60) Provisional application No. 62/035,291, filed on Aug. 8, 2014, provisional application No. 61/972,633, filed on Mar. 31, 2014.

(51) Int. Cl.
| | |
|---|---|
| *A61K 35/744* | (2015.01) |
| *A61K 9/00* | (2006.01) |
| *A61K 35/00* | (2006.01) |
| *A61K 35/74* | (2015.01) |
| *A61K 35/742* | (2015.01) |
| *A61K 39/00* | (2006.01) |
| *A61K 39/395* | (2006.01) |
| *C07K 16/28* | (2006.01) |

(52) U.S. Cl.
CPC .......... *A61K 35/744* (2013.01); *A61K 9/0019* (2013.01); *A61K 35/74* (2013.01); *A61K 35/742* (2013.01); *A61K 39/3955* (2013.01); *A61K 39/39558* (2013.01); *C07K 16/2803* (2013.01); *C07K 16/2818* (2013.01); *A61K 2035/115* (2013.01); *A61K 2039/505* (2013.01); *A61K 2039/54* (2013.01); *A61K 2039/545* (2013.01)

(58) Field of Classification Search
CPC .... A61K 35/744; A61K 9/0019; A61K 35/74; A61K 35/742; A61K 39/3955; A61K 39/39558; A61K 2035/115; A61K 2039/505; A61K 2039/54; A61K 2039/545; C07K 16/2803; C07K 16/2818
See application file for complete search history.

(56) References Cited

U.S. PATENT DOCUMENTS

| | | |
|---|---|---|
| 3,773,919 A | 11/1973 | Boswell et al. |
| 4,474,983 A | 10/1984 | Charbardes et al. |
| 4,485,045 A | 11/1984 | Regen |
| 4,544,545 A | 10/1985 | Ryan et al. |
| 4,816,567 A | 3/1989 | Cabilly et al. |
| 5,223,409 A | 6/1993 | Ladner et al. |
| 5,225,539 A | 7/1993 | Winter |
| 5,565,332 A | 10/1996 | Hoogenboom et al. |
| 5,698,520 A | 12/1997 | Honjo et al. |
| 5,733,743 A | 3/1998 | Johnson et al. |
| 5,798,229 A | 8/1998 | Strittmatter et al. |
| 5,871,907 A | 2/1999 | Winter et al. |
| 5,885,579 A | 3/1999 | Linsley et al. |
| 5,885,796 A | 3/1999 | Linsley et al. |
| 5,959,084 A | 9/1999 | Ring et al. |
| 5,968,510 A | 10/1999 | Linsley et al. |
| 5,977,318 A | 11/1999 | Linsley et al. |

(Continued)

FOREIGN PATENT DOCUMENTS

| | | |
|---|---|---|
| EP | 58481 | 8/1982 |
| EP | 102324 | 3/1984 |

(Continued)

OTHER PUBLICATIONS

Freshney (Culture of Animal Cells, a Manual of Basic Technique, Alan R. Liss, Inc., 1983, New York).*
Dermer (Bio/Technology, 1994, vol. 12 p. 320).*
Wang et al. (Exp. Opin. Biol. Ther. 2001; 1 (2): 277-290).*
Kelland (Eur. J. Cancer. Apr. 2004; 40 (6): 827-836).*
Gura (Science vol. 278 Nov. 1997 1041-1042).*
Voskoglou-Nomikos et al. (Clin. Cancer Res. Sep. 15, 2003; 9: 4227-4239).*
Saijo et al. (Cancer Sci. Oct. 2004; 95 (10): 772-776).*
Schuh (Toxicologic Pathology. 2004; 32 (Suppl. 1): 53-66).*
Bibby (Eur. J. Cancer. Apr. 2004; 40 (6): 852-857).*
Peterson et al. (Eur. J. Cancer. 2004; 40: 837-844).*

(Continued)

*Primary Examiner* — Robert A Zeman
(74) *Attorney, Agent, or Firm* — Bryan Cave Leighton Paisner LLP

(57) ABSTRACT

The presently disclosed subject matter provides methods and kits for treating solid tumors in a subject by using a combination of anti-CTLA-4 and/or anti-PD-1 antibodies with at least one member of the group consisting of a bacterium, bacterial product, and an immunoregulatory entity. In particular embodiments, the bacteria are toxin-depleted, anaerobic bacteria, such as *Clostridium novyi*-NT.

10 Claims, 23 Drawing Sheets

(56) References Cited

U.S. PATENT DOCUMENTS

| | | | |
|---|---|---|---|
| 2003/0086930 A1* | 5/2003 | Mueller | A61K 39/39541 424/155.1 |
| 2005/0079157 A1 | 4/2005 | Dang et al. | |
| 2011/0081354 A1 | 4/2011 | Korman et al. | |
| 2012/0251556 A1 | 10/2012 | Allison et al. | |
| 2013/0323167 A1 | 12/2013 | Vogelstein et al. | |
| 2016/0051597 A1* | 2/2016 | Saha | A61K 35/742 424/93.41 |

FOREIGN PATENT DOCUMENTS

| | | |
|---|---|---|
| EP | 125023 | 11/1984 |
| EP | 171496 | 2/1986 |
| EP | 173494 | 3/1986 |
| EP | 184187 | 6/1986 |
| WO | 198601533 | 3/1986 |
| WO | 199002809 | 3/1990 |
| WO | 1991017271 | 11/1991 |
| WO | 199201047 | 1/1992 |
| WO | 199215679 | 9/1992 |
| WO | 1992018619 | 10/1992 |
| WO | 199209690 | 11/1992 |
| WO | 1992020791 | 11/1992 |
| WO | 199301288 | 1/1993 |
| WO | 199402610 | 2/1994 |
| WO | 199503832 | 2/1995 |
| WO | 2006121168 | 11/2006 |
| WO | 2009100140 | 8/2009 |

OTHER PUBLICATIONS

Miller et al. (Cancer Immunology Research; vol. 4 No. 7, pp. 600-610) (Year: 2016).*
Meunst et al. (Breast Cancer Res. Treat. vol. 139, pp. 667-676).*
International Search Report for PCT/US2015/023633, mailed Jun. 19, 2015.
Written Opinion of the International Searching Authority for PCT/US2015/023633, mailed Jun. 19, 2015.
Diaz, Jr., L.A. et al., Pharmacologic and toxicologic evaluation of C. novyi-NT spores, Toxicological Sciences, 2005, vol. 88, No. 2, pp. 562-575.
Suarez et al. (2010) Neurocrit. Care 13:263-277.
Brunet et al. (1987) Nature 328:267-270.
Brunet et al. (1988) Immunol. Rev. 103-21-36.
Dariavach et al. (1988) Eur. J. Immunol. 18:1901-1905.
Lafage-Pochitaloff et al. (1990) Immunogenetics 31:198-201.
Linsley et al. (1992) J. Exp. Med. 176:1595-1604.
Wu et al. (1997) J. Exp. Med. 185:1327-1335.
Krummel et al. (1995) J. Exp. Med. 182:459-465.
Krummel et al. (1996) Int'l Immunol. 8:519-523.
Chambers et al. (1997) Immunity 7:885-895.
Walunas et al. (1994) Immunity 1:405-413.
Kearney (1995) J. Immunol. 155:1032-1036.
Leach (1996) Science 271:1734-1736.
Luhder (1998) J. Exp. Med. 187:427-432.
Chambers (1997) Curr. Opin. Immunol. 9:396-404.
Bluestone (1997) J. Immunol. 158:1989-1993.
Thompson (1997) Immunity 7:445-450.
Ishida et al. (1992) EMBO J. 11:3887.
Shinohara et al. (1994) Genomics 23:704.
Vivier and Daeron (1997) Immunol. Today 18:286.
Henry et al. (1999) Immunol. Today 20(6):285-8.
Agata et al. (1996) Int. Immunol. 8:765.
Nishimura et al. (1996) Int. Immunol. 8:773.
Freeman et al. (2000) J. Exp. Med. 192:1027.
Latchman et al. (2001) Nat. Immunol. 2:261.
Fallarino et al. (1998) J. Exp. Med. 188:205.
Higgins and Sharp (1989) Cabios 5:151-153.
Higgins et al. (1992) Comput. Appl. Biosci. 8:189-191.
Ward et al. (1989) Nature 341:544-546.
Bird et al. (1988) Science 242:423-426.
Huston et al. (1988) Proc. Natl. Acad Sci. USA 85:5879-5883.
Osbourn et al. (1998) Nature Biotechnology 16:778.
Holliger et al. (1993) Proc. Natl. Acad. Sci. USA 90:6444-6448.
Poljak et al. (1994) Structure 2:1121-1123.
Kipriyanov et al. (1995) Human Antibodies and Hybridomas 6:93-101.
Kipriyanov et al. (1994) Mol. Immunol. 31:1047-1058.
Kohler and Milstein (1975) Nature 256:495-497.
Brown et al. (1981) J. Immunol. 127:539-46.
Brown et al. (1980) J. Biol. Chem. 255:4980-83.
Yeh et al. (1979) Proc. Natl. Acad. Sci. 76:2927-2931.
Yeh et al. (1982) Int. J. Cancer 29:269-75.
Kozbor et al. (1983) Immunol. Today 4:72.
Kozbor et al. (1983) Immunology Today 4:,3 pp. 72-79.
Cole et al. (1985) Monoclonal Antibodies and Cancer Therapy, Alan R. Liss, Inc., pp. 77-96.
Kenneth, R. H. in Monoclonal Antibodies: A New Dimension in Biological Analyses, Plenum Publishing Corp., New York, N.Y. (1980).
Lerner (1981) Yale J. Biol. Med. 54:387-402.
Gefter et al. (1977) Somatic Cell Genet. 3:231-36.
Galfre et al. (1977) Nature 266:550-552.
Fuchs et al. (1991) Biotechnology (NY) 9:1369-1372.
Hay et al. (1992) Hum. Antibod. Hybridomas 3:81-85.
Huse et al. (1989) Science 246:1275-1281.
Griffiths et al. (1993) EMBO J. 12:725-734.
Hawkins et al. (1992) J. Mol. Biol. 226:889-896.
Clackson et al. (1991) Nature 352:624-628.
Gram et al. (1992) Proc. Natl. Acad. Sci. USA 89:3576-3580.
Garrard et al. (1991) Biotechnology (NY) 9:1373-1377.
Hoogenboom et al. (1991) Nucleic Acids Res. 19:4133-4137.
Barbas et al. (1991) Proc. Natl. Acad. Sci. USA 88:7978-7982.
McCafferty et al. (1990) Nature 348:552-554.
Better et al. (1988) Science 240:1041-1043.
Liu et al. (1987) Proc. Natl. Acad. Sci. USA 84:3439-3443.
Liu et al. (1987) J. Immunol. 139:3521-3526.
Sun et al. (1987) Proc. Natl. Acad. Sci. 84:214-218.
Nishimura et al. (1987) Cancer Res. 47:999-1005.
Wood et al. (1985) Nature 314:446-449.
Shaw et al. (1988)J Natl. Cancer Inst. 80:1553-1559.
Morrison, S. L. (1985) Science 229:1202-1207.
Oi et al. (1986) Biotechniques 4:214.
Jones et al. (1986) Nature 321:552-525.
Verhoeyan et al. (1988) Science 239:1534.
Beidler et al. (1988) J Immunol. 141:4053-4060.
Carlson (1988) Mol. Cell. Biol. 8:2638-2646.
Biocca et al. (1990) EMBO J. 9:101-108.
Werge et al. (1990) FEBS Lett. 274:193-198.
Carlson (1993) Proc. Mad Acad. Sci. USA 90:7427-7428.
Marasco et al. (1993) Proc. Natl. Acad. Sci. USA 90:7889-7893.
Biocca et al. (1994) Biotechnology (NY) 12:396-399.
Chen et al. (1994) Hum. Gene Ther. 5:595-601.
Duan et al. (1994) Proc. Natl. Acad. Sci. USA 91:5075-5079.
Chen et al. (1994) Proc. Natl. Acad. Sci. USA 91:5932-5936.
Beerli et al. (1994) J. Biol. Chem. 269:23931-23936.
Beerli et al. (1994) Biochem. Biophys. Res. Commun. 204:666-672.
Mhashilkar et al. (1995) EMBO J. 14:1542-1551.
Richardson et al. (1995) Proc. Natl. Acad. Sci. USA 92:3137-3141.
Hogan, et al., "Manipulating the Mouse Embryo: A Laboratory Manual," Cold Spring Harbor Laboratory.
Staerz et al. (1985) Nature 314:628.
Perez et al. (1985) Nature 316:354.
Staerz and Bevan (1986) Proc. Natl. Acad. Sci. USA, 83:1453.
Staerz and Bevan (1986) Immunol. Today 7:241.
Vogelstein et al. (2013) Science 339:1546-1558.
Joseph et al. (2014) Gene Chromosome Canc. 53:15-24.
Sharma et al. (2007) Nat. Rev. Cancer 7:169-181.
Chapman et al. (2011) New Engl. J Med 364:2507-2516.
Kwak et al. (2010) New Engl. J. Med 363:1693-1703.
Dang et al. (2004) Cancer Rio. Ther. 3:326-337.
Cheong et al. (2006) Science 314(5803):1308-1311.

(56) References Cited

OTHER PUBLICATIONS

Bettegowda el al. (2003) Proc. Natl. Acad. Sci. U.S.A. 100(25):15083-15088.
Sidman et al., Biopolymers 22:547, 1983.
Langer et al. (1981) J. Biomed. Mater. Res. 15:267.
Langer (1982), Chem. Tech. 12:98.
Epstein et al. (1985) Proc. Natl. Acad. Sci. U.S.A. 82:3688.
Hwang et al. (1980) Proc. Natl. Acad. Sci. U.S.A. 77:4030.
Chapman (2002) Adv. Drug Deliv. Rev. 54:531-545.
Cunningham-Rundles et al. (1992) J. Immunol. Meth. 152:177-190.
FC Kull et al. (1961) Appl. Environ. Microbiol. 9:6, 538-541.
Remington: The Science and Practice of Pharmacy (20th ed.) Lippincott, Williams and Wilkins (2000).
Krause and Van Etten (2005) New Engl. J. Med. 353:172-187.
Imai and Takaoka (2006) Nat. Rev.Cancer 6:714-727.
Sosman et al. (2012) New Engl. I. Med. 366:707-714.
Wilson and Hay (2011) Nat. Rev. Cancer 11:393-410.
Hanahan and Weinberg (2011) Cell 144:646-674.
Kerbel (2008) New Engl. J. Med. 358:2039-2049.
Chung and Ferrara (2011) Annu. Rev. Cell Dev. Bio. 27:563-584.
Baish et al. (2011) Proc. Natl. Acad. Sci. USA 108:1799-1803.
Horsman et al. (2012) Nat. Rev. Clin. Oncol. 9:674-687.
Coley(1910) Proc. Roy. Soc. Med. 3:1-48.
Coley (1991) Clin. Orthop. Relat. Res. 3-11.
Forbes (2010) Nat. Rev. Cancer 10:785-794.
Wei et al. (2008) Cancer Lett. 259:16-27.
Toso et al. (2002) J. Clin. Oncol. 20:142-152.
Thamm et al. (2005) Clin. Cancer Res. 11:4827-4834.
Nemunaitis et al. (2003) Cancer Gene Ther. 10:737-744.
Dang et al. (2001) Proc. Natl. Acad. Sci. USA 98:15155-15160.
Agrawal et al. (2004) Proc. Natl. Acad. Sci. USA 101:15172-15177.
Krick et al. (2012) Amer. J. Vet. Res. 73:112-118.
Diaz et al. (2005) Toxicol. Sci. 88:562-575.
Bai et al. (2011) Neuro-oncology 13:974-982.
Bettegowda et al. (2006) Nat. Biotechnol. 24:1573-1580.
Jones et al. (2010) Science 330:228-231.
Duke et al. (2014) Vet. Pathol.
Zarfoss et al. (2007) Vet. Pathol. 44:276-284.
Dennis et al. (2011) Vet. Pathol. 48:73-84.
Patnaik et al. (1984) Vet. Pathol. 21:469-474.
Smedley et al. (2011) Vet. Pathol. 48:54-72.
Nishida and Nakagawara (1964) J. Bacteriol. 88:1636-1640.
Paoloni and Khanna (2008) Nat. Rev. Cancer 8:147-156.
Vail and MacEwen (2000) Cancer Invest. 18:781-792.
Champiat et al. (2014) Oncoimmunology 3:e27817.
Barretina et al. (2010) Nat. Genet. 42:715-721.
Chmielecki et al. (2013) Nat. Genet. 45:131-132.

* cited by examiner

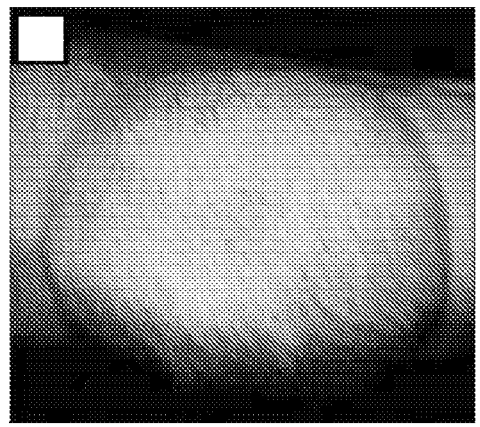
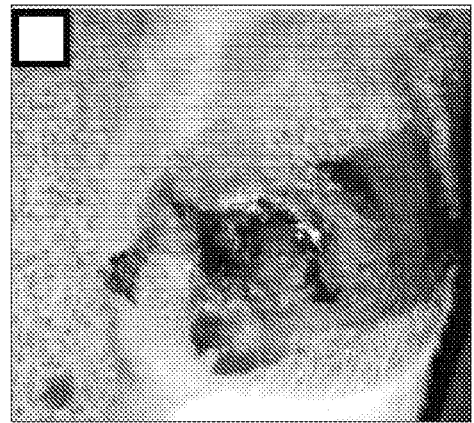
FIG. 6A    FIG. 6B
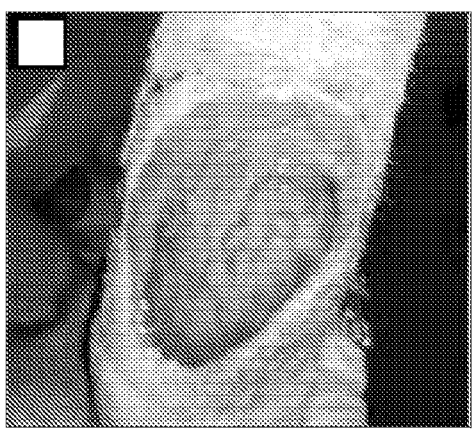
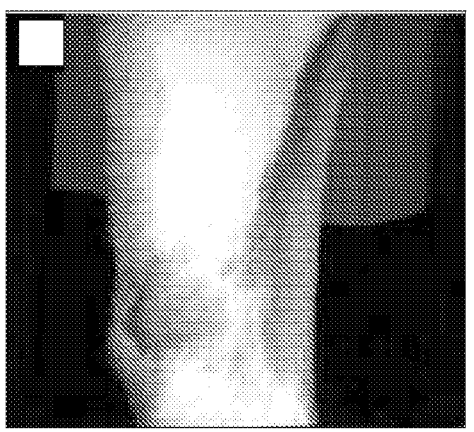
FIG. 6C    FIG. 6D
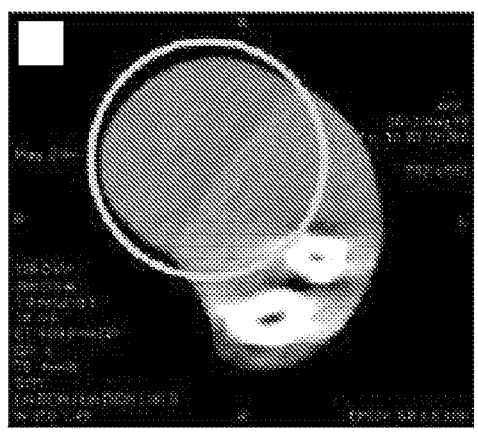
FIG. 6E    FIG. 6F

FIG. 10

| | 01-R02 | 04-R01 | 04-R02 | 04-R03 | 04-R08 | 11-R01 | 11-R02 | 11-R04 | 16-R02 | 16-R03 | MIN | MAX | AVERAGE |
|---|---|---|---|---|---|---|---|---|---|---|---|---|---|
| SAMPLE CHARACTERISTICS | | | | | | | | | | | | | |
| TUMOR TYPE | STS-PNST | STS-PNST | STS-PNST | STS-PNST | STS-PNST | STS-PNST | STS-PNST | STS-PBS | STS-MXS | STS-SCS | NA | NA | NA |
| TUMOR LOCATION | LEFT THORACIC FLANK | RIGHT MID MAXILLARY AREA | RIGHT METACARPUS | LEFT ANTEBRACHIUM | RIGHT HINDPAW | LEFT PINNA | LEFT STIFLE | RIGHT FOREPAW | LEFT THIGH | LEFT FOREPAW | NA | NA | NA |
| SAMPLE TYPE | FFPE | FFPE | FFPE | FFPE | FFPE | FFPE | FFPE | FFPE | FFPE | FFPE | NA | NA | NA |
| SAMPLE ACQUISITION | PRE-STUDY INITIATION | PRE-STUDY INITIATION | PRE-STUDY INITIATION | PRE-STUDY INITIATION | POST-STUDY INITIATION | POST-STUDY INITIATION | PRE-STUDY INITIATION | PRE-STUDY INITIATION | POST-STUDY INITIATION | PRE-STUDY INITIATION | NA | NA | NA |
| PATHOLOGICAL TUMOR PURITY | 80% | 80% | 90% | 90% | 90% | 90% | 80% | 70% | 70% | 70% | 70.0% | 90.0% | 81.0% |
| MUTATION BASED TUMOR PURITY | 29% | NA | 69% | 71% | 67% | 54% | 45% | 51% | 41% | 37% | 29.0% | 71.0% | 51.6% |
| SOURCE OF NORMAL DNA | BLOOD | BLOOD | BLOOD | BLOOD | BLOOD | BLOOD | BLOOD | BLOOD | BLOOD | BLOOD | NA | NA | NA |
| ANALYSIS CHARACTERISTICS | | | | | | | | | | | | | |
| ANALYSIS TYPE | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NEXT-GENERATION SEQUENCING | NA | NA | NA |
| ENRICHMENT APPROACH | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | IN SOLUTION DNA CAPTURE | NA | NA | NA |
| GENOME REGIONS ANALYZED | 30,194 CODING GENES | 30,194 CODING GENES | 30,194 CODING GENES | 30,194 CODING GENES | 30,194 CODING GENES | 30,194 CODING GENES | 30,194 CODING GENES | 30,194 CODING GENES | 30,194 CODING GENES | 30,194 CODING GENES | NA | NA | NA |
| SEQUENCED BASES | 32,893,252 BASES | 32,893,252 BASES | 32,893,252 BASES | 32,893,252 BASES | 32,893,252 BASES | 32,893,252 BASES | 32,893,252 BASES | 32,893,252 BASES | 32,893,252 BASES | 32,893,252 BASES | NA | NA | NA |
| SEQUENCE READ LENGTH | 100 BP | 100 BP | 100 BP | 100 BP | 100 BP | 100 BP | 100 BP | 100 BP | 100 BP | 100 BP | NA | NA | NA |

FIG. 10 (Cont.)

| SOMATIC (TUMOR-SPECIFIC) ALTERATIONS | | | | | | | | | | | | | |
|---|---|---|---|---|---|---|---|---|---|---|---|---|---|
| NUMBER OF SOMATIC SEQUENCE ALTERATIONS IDENTIFIED | 20 | 0 | 6 | 8 | 95 | 4 | 14 | 3 | 4 | 2 | 0 | 95 | 16 |
| NUMBER OF SOMATIC COPY NUMBER ALTERATIONS IDENTIFIED | 9 | 0 | 0 | 2 | 0 | 0 | 17 | 0 | 0 | 0 | 0 | 17 | 3 |
| OVERALL STATISTICS (TUMOR) | | | | | | | | | | | | | |
| SEQUENCED BASES MAPPED TO GENOME | 9,336,883,200 | 23,322,445,500 | 19,418,702,600 | 14,429,862,200 | 8,055,248,900 | 19,163,476,700 | 15,780,857,800 | 19,186,019,800 | 12,124,067,800 | 21,425,345,200 | 8,055,248,900 | 23,322,445,500 | 16,225,290,890 |
| SEQUENCED BASES MAPPED TO TARGET REGIONS | 3,967,568,909 | 9,068,570,137 | 8,491,584,341 | 6,089,590,437 | 3,317,956,697 | 8,571,289,371 | 10,233,153,813 | 11,459,270,433 | 4,838,071,422 | 9,789,715,947 | 3,317,956,697 | 11,459,270,433 | 7,398,677,151 |
| FRACTION OF SEQUENCED BASES MAPPED TO TARGET REGIONS | 42% | 39% | 44% | 42% | 41% | 45% | 65% | 60% | 40% | 46% | 38.9% | 64.8% | 46.4% |
| BASES IN TARGET REGIONS WITH AT LEAST 10 READS | 36,056,022,909 | 36,941,231 | 37,503,866 | 36,637,164 | 35,180,875 | 37,167,238 | 48,966,409 | 50,430,237 | 36,043,130 | 37,343,313 | 35,180,875 | 50,430,237 | 39,226,949 |
| FRACTION OF BASES IN TARGET REGIONS WITH AT LEAST 10 READS | 91% | 93% | 94% | 92% | 89% | 94% | 91% | 94% | 91% | 94% | 88.5% | 94.8% | 92.2% |

FIG. 10 (Cont.)

| OVERALL STATISTICS (NORMAL) | | | | | | | | | | | | | |
|---|---|---|---|---|---|---|---|---|---|---|---|---|---|
| SEQUENCED BASES MAPPED TO GENOME | 15,151,630,300 | 16,160,073,600 | 15,728,989,700 | 19,693,458,500 | 16,831,763,000 | 16,042,683,700 | 14,950,239,100 | 15,677,511,300 | 17,329,903,700 | 14,561,175,800 | 14,561,175,800 | 19,693,458,500 | 16,212,742,870 |
| SEQUENCED BASES MAPPED TO TARGET REGIONS | 5,777,414,557 | 6,222,258,939 | 6,167,005,020 | 7,318,085,121 | 6,370,985,466 | 6,245,786,511 | 7,394,567,092 | 8,201,336,539 | 6,882,015,752 | 5,586,179,511 | 5,586,179,511 | 8,201,336,539 | 6,616,561,451 |
| FRACTION OF SEQUENCED BASES MAPPED TO TARGET REGIONS | 38% | 39% | 39% | 37% | 38% | 39% | 49% | 52% | 40% | 38% | 37.2% | 52.3% | 41.0% |
| BASES IN TARGET REGIONS WITH AT LEAST 10 READS | 37,246,921 | 37,236,461 | 37,216,686 | 37,102,993 | 37,230,015 | 37,018,789 | 50,057,763 | 50,263,991 | 38,229,451 | 36,802,585 | 36,802,585 | 50,263,991 | 39,820,566 |
| FRACTION OF BASES IN TARGET REGIONS WITH AT LEAST 10 READS | 94% | 94% | 94% | 93% | 94% | 93% | 93% | 93% | 96% | 92% | 92.1% | 96.2% | 93.6% |

FIG. 10 (Cont.)

| SEQUENCED READS AT EACH BASE (TUMOR) | | | | | | | | | | | | |
|---|---|---|---|---|---|---|---|---|---|---|---|---|
| AVERAGE NUMBER OF TOTAL HIGH QUALITY SEQUENCES AT EACH BASE | 84 | 201 | 190 | 138 | 73 | 195 | 172 | 190 | 110 | 227 | 73 | 227 | 158 |
| AVERAGE NUMBER OF DISTINCT HIGH QUALITY SEQUENCES AT EACH BASE | 59 | 170 | 159 | 114 | 67 | 100174% | 127 | 160 | 99 | 202 | 59 | 202 | 133 |
| SEQUENCE READS AT EACH BASE (NORMAL) | | | | | | | | | | | | |
| AVERAGE NUMBER OF TOTAL HIGH QUALITY SEQUENCES AT EACH BASE | 140 | 152 | 150 | 178 | 152 | 154 | 130 | 145 | 168 | 137 | 130 | 178 | 151 |
| AVERAGE NUMBER OF DISTINCT HIGH QUALITY SEQUENCES AT EACH BASE | 120 | 133 | 127 | 149 | 130 | 125 | 112 | 127 | 152 | 121 | 112 | 152 | 130 |
| TUMOR/NORMAL MATCHING | | | | | | | | | | | | |
| GERMLINE SNPs PRESENT | 9,828 | 14,502 | 14,163 | 8,204 | 12,953 | 14,801 | 12,407 | 16,454 | 15,138 | 13,896 | 8,204 | 16,454 | 13,235 |
| PERCENT T/N MATCHING | 100% | 100% | 100% | 100% | 100% | 100% | 100% | 100% | 100% | 100% | 100% | 100% | 100% |
| SUMMARY DATA | | | | | | | | | | | | |
| MUTATIONS/Mb | 0.61 | 0.00 | 0.18 | 0.24 | 2.89 | 0.12 | 0.43 | 0.09 | 0.12 | 0.06 | 0.00 | 2.89 | 0.47 |
| CNAs/Mb | 0.27 | 0.00 | 0.00 | 0.06 | 0.00 | 0.00 | 0.52 | 0.00 | 0.00 | 0.00 | 0.00 | 0.52 | 0.09 |

STS-PNST — peripheral nerve sheath tumor; STS-FBS — fibrosarcoma; STS-MXS — myxosarcoma; STS — synovial cell sarcoma; T — tumor; N — normal; Mb — megabase; CNAs — copy number alterations; SNPs — single nucleotide polymorphisms; FFPE — formalin fixed paraffin embedded; NA — not applicable

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| 01-R02 | STS-PNST | ACD | ADRENOCORTICAL DYSPLASIA HOMOLOG (MOUSE) | ENSCAFT00000032411 | CHR5_84799806-84799806_C_A | 388P>H | SUBSTITUTION | NONSYNONYMOUS CODING | TGGCCNCCTGC | 13% |
| | | ADAMTS 5 | ADAM METALLOPEPTIDASE WITH THROMBOSPONDIN TYPE 1 MOTIF, 5 | ENSCAFT00000013627 | CHR31_25306205-25306205_G_A | 226H>Y | SUBSTITUTION | NONSYNONYMOUS CODING | CTGATNCTGCC | 13% |
| | | ADRB2 | BETA-2 ADRENERGIC RECEPTOR | ENSCAFT00000029135 | CHR4_63253706-63253706_C_T | 76C>Y | SUBSTITUTION | NONSYNONYMOUS CODING | CAGCANAGGCC | 12% |
| | | ATP7B | COPPER-TRANSPORTING ATPASE 2 | ENSCAFT00000006859 | CHR22_3160667-3160667_G_A | 1119V>M | SUBSTITUTION | NONSYNONYMOUS CODING | TGGGCNTGGCC | 20% |
| | | CDK14 | CYCLIN-DEPENDENT KINASE 14 | ENSCAFT00000003809 | CHR14_19522937-19522937_C_T | 102R>W | SUBSTITUTION | NONSYNONYMOUS CODING | TCAGGNGGCAC | 20% |
| | | IER5L | IMMEDIATE EARLY RESPONSE 5-LIKE | ENSCAFT00000031805 | CHR9_57855189-57855189_G_A | 20S>N | SUBSTITUTION | NONSYNONYMOUS CODING | CCACANCTCCC | 16% |
| | | IRS1 | INSULIN RECEPTOR SUBSTRATE 1 | ENSCAFT00000016522 | CHR25_42687032-42698.7032_C_T | 139S>N | SUBSTITUTION | NONSYNONYMOUS CODING | CCGAGNTGCCG | 11% |
| | | JAG1 | JAGGED 1 | ENSCAFT00000009074 | CHR24_14655994-14655994_G_A | 93S>N | SUBSTITUTION | NONSYNONYMOUS CODING | CTGTANCTTCG | 11% |
| | | JUNB | JUN B PROTO ONCOGENE | ENSCAFT00000027182 | CHR20_52362490-52362490_G_A | 77S>I | SUBSTITUTION | NONSYNONYMOUS CODING | GCTCCNATGAG | 14% |
| | | LMNA | LAMIN A/C | ENSCAFT00000026695 | CHR7_44690367-44690367_G_A | 64T>I | SUBSTITUTION | NONSYNONYMOUS CODING | ACTCGNTGATG | 15% |
| | | MADCAM1 | MUCOSAL ADDRESSIN CELL ADHESION MOLECULE 1 PRECURSOR | ENSCAFT00000031356 | CHR20_61126306-61126306_G | NA | DELETION | FRAMESHIFT | AAAGTNGGGGG | 27% |
| | | MEFV | MEDITERRANEAN FEVER | ENSCAFT00000037775 | CHR6_41024970-41024970_C_A | 673N>K | SUBSTITUTION | NONSYNONYMOUS CODING | GGAAANAAGAC | 26% |
| | | NOVEL GENE | ALDEHYDE DEHYDROGENASE | ENSCAFT00000017771 | CHR18_52833141-52833141_A_G | 250V>A | SUBSTITUTION | NONSYONYMOUS CODING | ACAGGNCGTAG | 11% |
| | | NRM | NURIM (NUCLEAR ENVELOPE MEMBRANE PROTEIN) | ENSCAFT00000000694 | CHR12_3488483-3488483_C_T | 524S>N | SUBSTITUTION | NONSYONYMOUS CODING | GGCAGNTGCGG | 11% |
| | | PIM1 | PROTO-ONCOGENE SERINE/THREONINE-PROTEIN KINASE PIM-1 | ENSCAFT00000002258 | CHR12_9213964-9213964_G_A | 73G>D | SUBSTITUTION | NONSYNONYMOUS CODING | CCCCGNCTCCT | 22% |
| | | PIM1 | PROTO-ONCOGENE | ENSCAFT00000 | CHR12_9214807- | 250H>Y | SUBSTITUTION | NONSYNONYMOUS | ACTGCNACAAC | 22% |

FIG. 11

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY 'N') | % MUTANT READS |
|---|---|---|---|---|---|---|---|---|---|---|
| | | | SERINE/THREONINE-PROTEIN KINASE PIM-1 | 00002258 | 9214807_C_T | | | CODING | | |
| | | PIM1 | PROTO-ONCOGENE SERINE/THREONINE-PROTEIN KINASE PIM-1 | ENSCAFT000 00002258 | CHR12_9214750-9214750_C_T | 231Q>X | SUBSTITUTION | NONSENSE | CCCTGNAGGAC | 20% |
| | | PTCH1 | PATCHED-LIKE PROTEIN 1 | ENSCAFT000 00001978 | CHR1_74305255-74305255_G_A | 73A>T | SUBSTITUTION | NONSYNONYMOUS CODING | GGAAANCTACT | 16% |
| | | TRPS1 | TRICHORHINOPHALANGEAL SYNDROME I | ENSCAFT000 00001274 | CHR13_18226051-18226051_C_T | 530S>N | SUBSTITUTION | NONSYONYMOUS CODING | CATGANTGTCC | 13% |
| | | ZFP36L1 | ZINC FINGER PROTEIN 36, C3H TYPE-LIKE 1 | ENSCAFT000 00026141 | CHR8_45703888-45703888_C_T | 145>N | SUBSTITUTION | NONSYONYMOUS CODING | CTTCGNTCAAG | 13% |
| 04-R02 | STS-PNST | KIAA1217 | UNCHARACTERIZED PROTEIN | ENSCAFT000 00006799 | CHR2_11859851-11859851_G_A | 356A>V | SUBSTITUTION | NONSYONYMOUS CODING | GAGAGNCGGGG | 45% |
| | | MFSD2B | MAJOR FACILITATOR SUPERFAMILY DOMAIN CONTAINING 2B | ENSCAFT000 00006341 | CHR17_21486565-21486565_C_T | 494R>C | SUBSTITUTION | NONSYONYMOUS CODING | GTGCANGTGGG | 42% |
| | | NOVEL GENE | UNCHARACTERIZED PROTEIN | ENSCAFT000 00030447 | CHRX_123930541-123930541_G_C | 327R>P | SUBSTITUTION | NONSYONYMOUS CODING | AGGGCNCCCG | 14% |
| | | SLC16A2 | SOLUTE CARRIER FAMILY 16, MEMBER 2 (THYROID HORMONE TRANSPORTER) | ENSCAFT000 00027229 | CHRX_60903455-60903455_G_A | 72A>T | SUBSTITUTION | NONSYONYMOUS CODING | CCTTCNCCTTT | 40% |
| | | TEP1 | TELOMERASE-ASSOCIATED PROTEIN 1 | ENSCAFT000 00008693 | CHR15_20729329-20729329_G_A | 1900L>F | SUBSTITUTION | NONSYONYMOUS CODING | CAGGANGCCCC | 42% |
| | | XPNPEP2 | X-PROLYL AMINOPEPTIDASE (AMINOPEPTIDASE P) 2, MEMBRANE-BOUND | ENSCAFT000 00029688 | CHRX_104033303-104033303_C_T | 502R>X | SUBSTITUTION | NONSENSE | CAGGGNGAATG | 25% |
| 04-R03 | STS-PNST | CCDC61 | COILED-COIL DOMAIN CONTAINING 61 | ENSCAFT000 00006986 | CHR1_112524782-104033303_C_T | NA | SUBSTITUTION | SPLICE SITE DONOR | CCCTANCTGGG | 41% |
| | | FAM83B | FAMILY WITH SEQUENCE SIMILARITY 83, MEMBER B | ENSCAFT000 00003643 | CHR12_25277449-25277449_G_T | 68V>F | SUBSTITUTION | NONSYONYMOUS CODING | AAAACNTCCAG | 39% |
| | | NOVEL GENE | UNCHARACTERIZED PROTEIN | ENSCAFT000 00006899 | CHR23_3005035-3005035_T_A | 32N>I | SUBSTITUTION | NONSYONYMOUS CODING | GGTCANTATTA | 34% |
| | | NOVEL GENE | UNCHARACTERIZED PROTEIN | ENSCAFT000 00028936 | CHR20_55267898-55267898_C_T | 323R>X | SUBSTITUTION | NONSENSE | AGGAGNCACGC | 17% |
| | | NUP210 | NUCLEOPORIN 210kDa | ENSCAFT000 | CHR20_6644043- | 1627P>T | SUBSTITUTION | NONSYONYMOUS | GCCCGNGATGG | 38% |

*FIG. 11 (Cont.)*

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACID (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | | | 00007053 | 6644043_G_T | | | CODING | | |
| | | PLMN | PLASMINOGEN PLASMIN HEAVY CHAIN A PLASMIN LIGHT CHAIN B | ENSCAFT000 00001179 | CHR1_52549843-52549843_C_T | 598G>E | SUBSTITUTION | NONSYONYMOUS CODING | CGCACNCACCT | 28% |
| | | UFSP2 | UFM1-SPECIFIC PEPTIDASE 2 | ENSCAFT000 00012105 | CHR16_48180970-48180970_T_G | 271L>R | SUBSTITUTION | NONSYONYMOUS CODING | TIACCNCAATC | 61% |
| | | ZNFX1 | ZINC FINGER, NFX1-TYPE CONTAINING 1 | ENSCAFT000 00018115 | CHR24_38909185-38909185_T_G | 1195S>L | SUBSTITUTION | NONSYONYMOUS CODING | AACAANGTCAT | 34% |
| 04-R08 | STS-PNST | A1ILJ0 | SERPIN PEPTIDASE INHIBITOR, CLAD A (ALPHA-1 ANTIPROTEINASE, ANTITRYPSIN), MEMBER 1 PRECURSOR | ENSCAFT000 00036554 | CHR8_66432888-66432888_C_T | 194_D_N | SUBSTITUTION | NONSYONYMOUS CODING | GACATNCTCTA | 42% |
| | | AASS | AMINOADIPATE-SEMIALDEHYDE SYNTHASE | ENSCAFT000 00005673 | CHR14_62956632-62956632_C_T | 66G>S | SUBSTITUTION | NONSYONYMOUS CODING | AATGCNACCAG | 62% |
| | | ABCB10 | ATP-BINDING CASSETTE, SUB-FAMILY B (MDR/TAP), MEMBER 10 | ENSCAFT000 00019279 | CHR4_12734254-12734254_C_T | 495R>C | SUBSTITUTION | NONSYONYMOUS CODING | CAGCTNGCCCA | 47% |
| | | ACTL9 | ACTIN-LIKE 9 | ENSCAFT000 00029470 | CHR20_56179685-56179685_G_A | 363P>S | SUBSTITUTION | NONSYONYMOUS CODING | GGGGGNCAGGC | 37% |
| | | ADAM7 | ADAM METALLOPEPTIDASE DOMAIN 7 | ENSCAFT000 00014408 | CHR25_35952270-35952270_C_T | 473E>K | SUBSTITUTION | NONSYONYMOUS CODING | CACTTNAGGAA | 31% |
| | | ADCYAP1R1 | ADENYLATE CYCLASE ACTIVATING POLYPEPTIDE 1 (PITUITARY) RECEPTOR TYPE I | ENSCAFT000 00005018 | CHR14_46708954-46708954_C_T | 448S>F | SUBSTITUTION | NONSYONYMOUS CODING | GGGCTNCTTCC | 63% |
| | | ALDH7A1 | ALDEHYDE DEHYDROGENASE 7 FAMILY, MEMBER A 1 | ENSCAFT000 000000904 | CHR11_18836811-18836811_G_A | 523T>I | SUBSTITUTION | NONSYONYMOUS CODING | TGATANTACTA | 30% |
| | | ANKLE1 | ANKYRIN REPEAT AND LEM DOMAIN CONTAINING 1 | ENSCAFT000 00024464 | CHR20_48444251-48444251_G_A | 74Q_X | SUBSTITUTION | NONSENSE | CTCCTNGTCTC | 27% |
| | | ARMC9 | ARMADILLO REPEAT CONTAINING 9 | ENSCAFT000 00017508 | CHR25_46161506-46161506_C_T | 296T>I | SUBSTITUTION | NONSYONYMOUS CODING | TTCAANCATGT | 29% |
| | | ASPM | ABNORMAL SPINDLE- | ENSCAFT000 | CHR7_8578487- | 1156L>F | SUBSTITUTION | NONSYONYMOUS | CATTTNTTTGC | 20% |

*FIG. 11 (Cont.)*

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | | LIKE MICROCEPHALY-ASSOCIATED PROTEIN HOMOLOG | 00018114 | 8578487_C_T | | | CODING | | |
| | | ATP13A1 | ATPASE TYPE 13A 1 | ENSCAFT000 00022481 | CHR20_46627633-46627633_C_T | 633S>F | SUBSTITUTION | NONSYNONYMOUS CODING | AATGTNCGTGC | 20% |
| | | ATP2B3 | ATPASE, CA++ TRANSPORTING, PLASMA MEMBRANE 3 | ENSCAFT000 00030531 | CHRX_124404772-124404772_C_T | 22P>L | SUBSTITUTION | NONSYNONYMOUS CODING | GGCCCNCCATG | 19% |
| | | B4EY10 | TRYPTOPHAN 5-HYDROXYLASE 1 | ENSCAFT000 00014485 | CHR21_43753174-43753174_C_T | 98R>Q | SUBSTITUTION | NONSYNONYMOUS CODING | ATTTTNGGGAC | 47% |
| | | BCAR1 | BREAST CANCER ANTI-ESTROGEN RESISTANCE 1 | ENSCAFT000 00031962 | CHR5_78491554-78491554_C_T | 150P>S | SUBSTITUTION | NONSYNONYMOUS CODING | AGATGNCCCAT | 28% |
| | | BOD1L1 | BIORIENTATION OF CHROMOSOMES IN CELL DIVISION 1-LIKE 1 | ENSCAFT000 00024431 | CHR3_69317598-69317598_C_T | 2128P>S | SUBSTITUTION | NONSYNONYMOUS CODING | AACTCNCTGCG | 29% |
| | | BRDT | BROMODOMAIN, TESTIS-SPECIFIC | ENSCAFT000 00032118 | CHR6_59977191-59977191_C_T | 874E>K | SUBSTITUTION | NONSYNONYMOUS CODING | ATTTTNTTGAA | 50% |
| | | BRE | BRAIN AND REPRODUCTIVE ORGAN EXPRESSED (TNFRSF1A MODULATOR) | ENSCAFT000 00008397 | CHR17_25386278-25386278_G_T | 372Q>H | SUBSTITUTION | NONSYNONYMOUS CODING | AACCANCCTC | 36% |
| | | C11 OR F80 | CHROMOSOME 11 OPEN READING FRAME 80 | ENSCAFT000 00019460 | CHR18_53566794-53566794_G_A | 206P>L | SUBSTITUTION | NONSYNONYMOUS CODING | TCAGANGCAGA | 45% |
| | | C1 OR F168 | CHROMOSOME 1 OPEN READING FROM 168 | ENSCAFT000 00030112 | CHR5_55715053-55715053_C_T | 219T>I | SUBSTITUTION | NONSYNONYMOUS CODING | AGAAANCCCTC | 26% |
| | | C6 OR F211 | CHROMOSOME 6 OPEN READING FRAME 211 | ENSCAFT000 00000674 | CHR1_44848305-44848305_C_T | 38R>X | SUBSTITUTION | NONSENSE | TGCATNGACAT | 32% |
| | | CABP2 | CALCIUM BINDING PROTEIN 2 | ENSCAFT000 00018054 | CHR18_52987478-52987478_G_A | 67G>E | SUBSTITUTION | NONSYNONYMOUS CODING | AGTGGNGCCGG | 35% |
| | | CEP250 | CENTROSOMAL PROTEIN 250KDA | ENSCAFT000 00012850 | CHR24_27405113-27405113_C_T | 550L>F | SUBSTITUTION | NONSYNONYMOUS CODING | TCATTNTTCGG | 60% |
| | | CSMD1 | CUB AND SUSHI MULTIPLE DOMAINS 1 | ENSCAFT000 00013885 | CHR16_58244318-58244318_G_A | 1551S>F | SUBSTITUTION | NONSYNONYMOUS CODING | TCTGCNAATGG | 48% |
| 04-R08 | STS-PNST | CSMD2 | CUB AND SUSHI MULTIPLE DOMAINS 2 | ENSCAFT000 00005882 | CHR15_11028241-11028241_C_T | 728S>L | SUBSTITUTION | NONSYNONYMOUS CODING | GACTTNGCCCA | 18% |
| | | DCDC2 | DOUBLE CORTIN | ENSCAFT000 | CHR35_25388917- | 192G>E | SUBSTITUTION | NONSYNONYMOUS | GTTTTNCTCT | 54% |

*FIG. 11(Cont.)*

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | | DOMAIN CONTAINING 2 | 00016283 | 25388917_C_T | | | CODING | | |
| | | DNMT3B | DNA (CYTOSINE-5-)-METHYLTRANSFERASE 3 BETA | ENSCAFT000 00011678 | CHR24_25068698-25068698_C_T | 61S>F | SUBSTITUTION | NONSYNONYMOUS CODING | ATTGTNCAAGA | 26% |
| | | EMR2 | EGF-LIKE MODULE-CONTAINING MUCIN-LIKE HORMONE RECEPTOR-LIKE 2 PRECURSOR | ENSCAFT000 00025982 | CHR20_50969425-50969425_C_T | 75S>N | SUBSTITUTION | NONSYNONYMOUS CODING | GGCTGNTGAAG | 43% |
| | | EXOC3L1 | EXOCYST COMPLEX COMPONENT 3-LIKE 1 | ENSCAFT000 00032455 | CHR5_85189666-85189666_G_A | 539R>K | SUBSTITUTION | NONSYNONYMOUS CODING | GGTGANAGTCC | 46% |
| | | FCRLB | F C RECEPTOR-LIKE A | ENSCAFT000 00020702 | CHR38_23962108-23962108_C_A | 21A>S | SUBSTITUTION | NONSYNONYMOUS CODING | GGCTGNCCAGA | 14% |
| | | FLRT1 | FIBRONECTIN LEUCINE RICH TRANSMEMBRANE PROTEIN 1 | ENSCAFT000 00023385 | CHR18_55953743-55953743_C_T | 616G>D | SUBSTITUTION | NONSYNONYMOUS CODING | CGGGGNCCGG | 31% |
| | | FMR1 | FRAGILE X MENTAL RETARDATION 1 | ENSCAFT000 00030311 | CHRX_119344462-119344462_G_A | 331E>K | SUBSTITUTION | NONSYNONYMOUS CODING | CCAAGNAAATT | 24% |
| | | FMR1 | FRAGILE X MENTAL RETARDATION 1 | ENSCAFT000 00030311 | CHRX_119344481-119344481_C_T | 337S>F | SUBSTITUTION | NONSYNONYMOUS CODING | AAATTNCCTAC | 20% |
| | | FSCN3 | FASCIN HOMOLOG 3, ACTIN-BUNDLING PROTEIN, TESTICULAR (STRONGYLOCENTROTUS PURPURATUS) | ENSCAFT000 00002697 | CHR14_11685668-11685668_G_A | 310R>C | SUBSTITUTION | NONSYNONYMOUS CODING | TGCANAAGCT | 48% |
| | | FUT9 | ALPHA-(1,3)-FUCOSYLTRANSFERASE | ENSCAFT000 00005507 | CHR12_57775088-57775088_G_A | 331E>K | SUBSTITUTION | NONSYNONYMOUS CODING | TTTGGNAATCA | 28% |
| | | FXYD3 | FXYD DOMAIN CONTAINING ION TRANSPORT REGULATOR 3 | ENSCAFT000 00011413 | CHR1_120363321-120363321_C_T | NA | SUBSTITUTION | SPLICE SITE DONOR | TCTCANCATAG | 88% |
| | | GPR126 | G PROTEIN-COUPLED RECEPTOR 126 | ENSCAFT000 00000457 | CHR1_37098753-37098753_C_T | 415S>F | SUBSTITUTION | NONSYNONYMOUS CODING | AATTTNCATAG | 24% |
| | | GPR128 | G PROTEIN-COUPLED RECEPTOR 128 | ENSCAFT000 00014844 | CHR33_10191962-10191962_C_T | 34R>W | SUBSTITUTION | NONSYNONYMOUS CODING | AAGGANGGAGG | 33% |
| | | GPR82 | G PROTEIN-COUPLED RECEPTOR 82 | ENSCAFT000 00022877 | CHRX_36056596-36056596_C_T | 213S>L | SUBSTITUTION | NONSYNONYMOUS CODING | ATTTTNATTTT | 32% |
| | | GRM6 | GLUTAMATE RECEPTOR, METABOTROPIC 6 | ENSCAFT000 00000509 | CHR11_5596380-5596380_C_T | 523P>L | SUBSTITUTION | NONSYNONYMOUS CODING | CCTCCNCTGTG | 53% |
| | | GSX1 | GS HOMEOBOX 1 | ENSCAFT000 00010870 | CHR25_14841844-14841844_C_T | NA | SUBSTITUTION | SPLICE SITE ACCEPTOR | GCTGTNTGGAG | 36% |

*FIG. 11 (Cont.)*

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACID (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | GTF2I | GENERAL TRANSCRIPTION FACTOR IIi | ENSCAFT00000038018 | CHR6_8807549-8807549_G_A | 145Q>X | SUBSTITUTION | NONSENSE | AGACTNATCTC | 43% |
| | | HDAC8 | HISTONE DEACETYLASE 8 | ENSCAFT00000027174 | CHRX_59408793-59408793_G_A | 359S>F | SUBSTITUTION | NONSYNONYMOUS CODING | GGGAANAGAAG | 71% |
| | | HECTD4 | HECT DOMAIN CONTAINING E3 UBIQUITIN PROTEIN LIGASE 4 | ENSCAFT00000014076 | CHR26_12845851-12845851_C_T | 541R>Q | SUBSTITUTION | NONSYNONYMOUS CODING | CTTCCNGCTTG | 38% |
| | | K1C10 | KERATIN, TYPE I CYTOSKELETAL 10 | ENSCAFT00000025391 | CHR9_25194405-25194405_G_A | 316E>K | SUBSTITUTION | NONSYNONYMOUS CODING | AATACNAACAA | 30% |
| | | KCNG3 | POTASSIUM VOLTAGE-GATED CHANNEL, SUBFAMILY G, MEMBER 3 | ENSCAFT00000035514 | CHR17_37144629-37144629_G_A | 366S>F | SUBSTITUTION | NONSYNONYMOUS CODING | TGTTGNATGTT | 43% |
| | | KIF25 | KINESIN FAMILY MEMBER 25 | ENSCAFT00000001345 | CHR1_58634208-58634208_G_A | 509E>K | SUBSTITUTION | NONSYNONYMOUS CODING | TGTCGNAGCGC | 33% |
| | | LAMB2 | LAMININ, BETA 2 (LAMININ S) | ENSCAFT00000018765 | CHR20_43058275-43058275_C_T | 1054P>L | SUBSTITUTION | NONSYNONYMOUS CODING | GTGCCNGTCCA | 38% |
| | | LIMK1 | LIM DOMAIN KINASE 1 | ENSCAFT00000019799 | CHR6_9274167-9274167_G_A | 222R>W | SUBSTITUTION | NONSYNONYMOUS CODING | GATCCNGTCTC | 60% |
| | | LY9 | LYMPHOCYTE ANTIGEN 9 | ENSCAFT00000020056 | CHR38_24536297-24536297_C_T | 263E>K | SUBSTITUTION | NONSYNONYMOUS CODING | CGACTNCCCCA | 58% |
| | | MBD5 | METHYL-CPG BINDING DOMAIN PROTEIN 5 | ENSCAFT00000008917 | CHR19_53239621-53239621_C_T | 1109P>L | SUBSTITUTION | NONSYNONYMOUS CODING | TGGTCNAGCTA | 32% |
| | | MLF1 | MYELOID LEUKEMIA FACTOR 1 | ENSCAFT00000014162 | CHR23_54989572-54989572_C_T | 164A>V | SUBSTITUTION | NONSYNONYMOUS CODING | CCGAGNTCATG | 33% |
| | | NELL1 | NEL-LIKE 1 (CHICKEN) | ENSCAFT00000015919 | CHR21_46027895-46027895_G_A | 105E>K | SUBSTITUTION | NONSYNONYMOUS CODING | CTGTCNAATGT | 24% |
| | | NF1 | NEUROFIBROMIN 1 | ENSCAFT00000029945 | CHR9_44834512-44834512_G_A | 1933P>S | SUBSTITUTION | NONSYNONYMOUS CODING | CCACGNAGTCA | 48% |
| | | NOVEL GENE | UNCHARACTERIZED PROTEIN | ENSCAFT00000021819 | CHR27_39478508-39478508_G_A | 1291E>K | SUBSTITUTION | NONSYNONYMOUS CODING | GTTCTNAACTA | 36% |
| | | NOVEL GENE | UNCHARACTERIZED PROTEIN | ENSCAFT00000004310 | CHR1_106460436-106460436_G_A | 314E>K | SUBSTITUTION | NONSYNONYMOUS CODING | GGGAGNAGAAA | 47% |
| | | NOVEL GENE | UNCHARACTERIZED PROTEIN | ENSCAFT00000028222 | CHR6_27157711-27157711_C_T | 319M>I | SUBSTITUTION | NONSYNONYMOUS CODING | AAAATNATGCA | 39% |
| | | NOVEL GENE | UNCHARACTERIZED PROTEIN | ENSCAFT00000027418 | CHR8_56643270-56643270_G_A | 395R>C | SUBSTITUTION | NONSYNONYMOUS CODING | TAAACNATCAG | 38% |
| | | NOVEL GENE | UNCHARACTERIZED PROTEIN | ENSCAFT00000012946 | CHR25_30547894-30547894_G_A | 397D>N | SUBSTITUTION | NONSYNONYMOUS CODING | GGCATNATGGC | 31% |
| | | NOVEL | UNCHARACTERIZED | ENSCAFT00000 | CHRX_115997637- | 6E>K | SUBSTITUTION | NONSYNONYMOUS | CAATTNGCCAG | 41% |

FIG. 11 (Cont.)

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | GENE | PROTEIN | 00030235 | 115997437_C_T | | | CODING | | |
| | | NOVEL GENE | UNCHARACTERIZED PROTEIN | ENSCAFT000 00024549 | CHR6_14378075-14378075_G_A | 734S>F | SUBSTITUTION | NONSYNONYMOUS CODING | TTTTGNAAATT | 36% |
| | | NOVEL GENE | UNCHARACTERIZED PROTEIN | ENSCAFT000 00009040 | CHR1_116977163-116977163_C_A | 56E>X | SUBSTITUTION | NONSENSE | CACTTNGGAGC | 17% |
| | | NTN5 | NETRIN 5 | ENSCAFT000 00006331 | CHR1_110537423-110537423_G_A | 259W>X | SUBSTITUTION | NONSENSE | CTTCTNGAGGG | 17% |
| | | NUP210L | NUCLEOPORIN 210KDA-LIKE | ENSCAFT000 00027524 | CHR7_46057921-46057921_C_T | 287P>S | SUBSTITUTION | NONSYNONYMOUS CODING | GATTTNCTCTG | 25% |
| | | NVL | NUCLEAR VCP-LIKE | ENSCAFT000 00025949 | CHR7_43088033-43088033_C_T | 783S>L | SUBSTITUTION | NONSYNONYMOUS CODING | CTACTNGTGAG | 16% |
| | | OLFM4 | OLFACTOMEDIN 4 | ENSCAFT000 00038323 | CHR22_13020301-13020301_G_C | 245D>H | SUBSTITUTION | NONSYNONYMOUS CODING | GTTCANCTCAA | 26% |
| | | OR11H4 | OLFACTORY RECEPTOR, FAMILY 11, SUBFAMILY H, MEMBER 4 | ENSCAFT000 00009634 | CHR15_20603710-20603710_G_A | 352M>I | SUBSTITUTION | NONSYNONYMOUS CODING | GACATNAAATT | 33% |
| | | OR11L1 | OLFACTORY RECEPTOR, FAMILY 11, SUBFAMILY L, MEMBER 1 | ENSCAFT000 00039246 | CHR14_456143-456143_C_T | 164S>F | SUBSTITUTION | NONSYNONYMOUS CODING | GATTTNCAAGT | 25% |
| | | PEPB | PEPSIN B PRECURSOR | ENSCAFT000 00031388 | CHR6_43778633-43778633_G_A | 367D>N | SUBSTITUTION | NONSYNONYMOUS CODING | TGGGANATGTC | 14% |
| | | PHKA2 | PHOSPHORYLASE KINASE, ALPHA 2 (LIVER) | ENSCAFT000 00020564 | CHRX_14879295-14879295_C_T | NA | SUBSTITUTION | SLICE SITE DONOR | ACTTANTTTAT | 46% |
| | | PKHD1 | POLYCYSTIC KIDNEY AND HEPATIC DISEASE 1 (AUTOSOMAL RECESSIVE) | ENSCAFT000 00003416 | CHR12_22675987-22675987_G_A | 1323S>L | SUBSTITUTION | NONSYNONYMOUS CODING | TCACTNAGTTG | 38% |
| | | PRDM2 | PR DOMAIN CONTAINING 2, WITH ZNF DOMAIN | ENSCAFT000 00025940 | CHR2_86311966-86311966_G_A | 1366P>S | SUBSTITUTION | NONSYNONYMOUS CODING | GGACGNCAGCG | 31% |
| | | PTPRO | PROTEIN TYROSINE PHOSPHATASE, RECEPTOR TYPE, O | ENSCAFT000 00020369 | CHR27_34189070-34189070_C_T | 309E>K | SUBSTITUTION | NONSYNONYMOUS CODING | TTTTTNCGTCT | 57% |
| | | PTPRZ1 | PROTEIN TYROSINE PHOSPHATASE, RECEPTOR-TYPE, Z POLYPEPTIDE 1 | ENSCAFT000 00005646 | CHR14_62891929-62891929_T_C | 1733L>P | SUBSTITUTION | NONSYNONYMOUS CODING | TAAACNTGCAC | 11% |
| | | Q28302 | UNCHARACTERIZED PROTEIN | ENSCAFT000 00035111 | CHR20_54398781-54398781_C_T | 202L>F | SUBSTITUTION | NONSYNONYMOUS CODING | AACTCNTCAAC | 34% |
| | | Q3B1Y3 | MULTIDRUG RESISTANCE PROTEIN 3 | ENSCAFT000 00027259 | CHR9_29903253-29903253_G_A | 761R>Q | SUBSTITUTION | NONSYNONYMOUS CODING | CCAGCNACAGC | 47% |

FIG. 11 (Cont.)

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | Q8HYR2 | UNCHARACTERIZED PROTEIN | ENSCAFT00000019633 | CHR27_29388021-29388021_A_T | 166I>F | SUBSTITUTION | NONSYNONYMOUS CODING | GAAATNTTATA | 59% |
| | | RCC2 | REGULATOR OF CHROMOSOME CONDENSATION 2 | ENSCAFT00000024961 | CHR2_83776440-83776440_C_T | 309P>L | SUBSTITUTION | NONSYNONYMOUS CODING | GGTCCNCCGGC | 46% |
| | | RP1 | OXYGEN-REGULATED PROTEIN 1 | ENSCAFT00000011204 | CHR29_9140829-9140829_G_A | 1861E>K | SUBSTITUTION | NONSYNONYMOUS CODING | AATCANAAAGA | 30% |
| | | RTKN2 | RHOTEKIN 2 | ENSCAFT00000020670 | CHR4_17382177-17382177_G_A | 602S>L | SUBSTITUTION | NONSYNONYMOUS CODING | GCCATNATCTG | 29% |
| | | SAMD7 | STERILE ALPHA MOTIF DOMAIN CONTAINING 7 | ENSCAFT00000023423 | CHR34_37539386-37539386_G_A | 369R>Q | SUBSTITUTION | NONSYNONYMOUS CODING | TCTTCNAAGCA | 29% |
| | | SLAF1 | SIGNALING LYMPHOCYTIC ACTIVATION MOLECULE | ENSCAFT00000019982 | CHR38_24663637-24663637_C_T | 233S>L | SUBSTITUTION | NONSYNONYMOUS CODING | GTCTTNGGGTG | 53% |
| | | SLC47A2 | SOLUTE CARRIER FAMILY 47, MEMBER 2 | ENSCAFT00000036298 | CHR5_43495248-43495248_C_T | 83S>F | SUBSTITUTION | NONSYNONYMOUS CODING | AGTTTNCATAG | 38% |
| | | SULT4A1 | SULFOTRANSFERASE FAMILY 4A, MEMBER 1 | ENSCAFT00000035674 | CHR10_24862764-24862764_G_A | 72M>I | SUBSTITUTION | NONSYNONYMOUS CODING | TTGATNAACAT | 26% |
| | | TAF7L | TAF7-LIKE RNA POLYMERASE II, TATA BOX BINDING PROTEIN (TBP)-ASSOCIATED FACTOR, 50KDA | ENSCAFT00000027954 | CHRX_78291782-78291782_C_T | 366E>K | SUBSTITUTION | NONSYNONYMOUS CODING | CTTTTNATAAT | 41% |
| | | TBC1D15 | TBC1 DOMAIN FAMILY, MEMBER 15 | ENSCAFT00000000735 | CHR10_16382190-16382190_C_T | 176S>F | SUBSTITUTION | NONSYNONYMOUS CODING | TGACTNTCTTG | 30% |
| | | TLR1 | TOLL-LIKE RECEPTOR 1 PRECURSOR | ENSCAFT00000037196 | CHR3_76368607-76368607_G_A | 234W>X | SUBSTITUTION | NONSENSE | GGATGNTCTTA | 30% |
| | | TMEM74 | TRANSMEMBRANE PROTEIN 74 | ENSCAFT00000001114 | CHR13_12451185-12451185_G_A | 61R>C | SUBSTITUTION | NONSYNONYMOUS CODING | AGGGCNAAGTT | 34% |
| | | TOM1 | TARGET OF MYB1 (CHICKEN) | ENSCAFT00000002700 | CHR10_31874137-31874137_A_C | 50V>G | SUBSTITUTION | NONSYNONYMOUS CODING | GCATCNCCTCA | 36% |
| | | TRIM58 | TRIPARTITE MOTIF CONTAINING 58 | ENSCAFT00000001915 | CHR14_4533386-4533386_G_C | 455T>R | SUBSTITUTION | NONSYNONYMOUS CODING | CGTTTNTTACA | 23% |
| | | TRIM66 | TRIPARTITE MOTIF CONTAINING 66 | ENSCAFT00000011106 | CHR21_35253035-35253035_G_A | 662L>F | SUBSTITUTION | NONSYNONYMOUS CODING | TGGGANAGGCG | 43% |
| | | TTN | TITIN | ENSCAFT00000022319 | CHR36_25212813-25212813_C_T | 25277E>K | SUBSTITUTION | NONSYNONYMOUS CODING | ACTTTNTTTAA | 31% |
| | | TTN | TITIN | ENSCAFT00000022319 | CHR36_25208898-25208898_G_A | 26582P>S | SUBSTITUTION | NONSYNONYMOUS CODING | GACCGNTTCGC | 36% |

FIG. 11 (Cont.)

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACIDE (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | TTN | TITIN | ENSCAFT00000022319 | CHR36_25207752-25207752_C_T | 26964E>K | SUBSTITUTION | NONSYNONYMOUS CODING | GTTTTNTGCAT | 32% |
| | | TTN | TITIN | ENSCAFT00000022319 | CHR36_25363681-25363681_C_T | 6209E>K | SUBSTITUTION | NONSYNONYMOUS CODING | GTTCTNGTGAC | 32% |
| | | USP45 | UBIQUITIN SPECIFIC PEPTIDASE 45 | ENSCAFT00000005638 | CHR12_60682412-60682412_G_A | 232P>S | SUBSTITUTION | NONSYNONYMOUS CODING | GGGAGNAAAAA | 43% |
| 11-R01 | STS-PNST | ACTN2 | ACTININ, ALPHA 2 | ENSCAFT00000017321 | CHR4_6385028-6385028_C_T | 90G>E | SUBSTITUTION | NONSYNONYMOUS CODING | TTTTTNCTCGG | 24% |
| | | GPR139 | G PROTEIN-COUPLED RECEPTOR 139 | ENSCAFT00000028634 | CHR6_28316728-28316728_C_T | 132P>L | SUBSTITUTION | NONSYNONYMOUS CODING | CCACCNTGCTCA | 27% |
| | | KCNJ16 | POTASSIUM INWARDLY-RECTIFYING CHANNEL, SUBFAMILY J, MEMBER 16 | ENSCAFT00000017085 | CHR9_19566120-19566120_G_T | 56>C | SUBSTITUTION | NONSYNONYMOUS CODING | ATTACNGCAGC | 26% |
| | | KCNJ5 | POTASSIUM INWARDLY RECTIFYING CHANNEL, SUBFAMILY J, MEMBER 5 | ENSCAFT00000016271 | CHR5_8746471-8746471_C_G | 116G>R | SUBSTITUTION | NONSYNONYMOUS CODING | ATCACNCCGGA | 32% |
| 11-R02 | STS-PNST | AFAP1L1 | ACTIN FILAMENT ASSOCIATED PROTEIN 1-LIKE 1 | ENSCAFT00000029078 | CHR4_62838379-62838379_G_A | 425S>F | SUBSTITUTION | NONSYNONYMOUS CODING | TCTTGNAGAAG | 25% |
| | | ATP7B | COPPER-TRANSPORTING ATPASE 2 | ENSCAFT00000006859 | CHR22_3134952-3134952_A_C | 288K>Q | SUBSTITUTION | NONSYNONYMOUS CODING | ACCCANAGATG | 20% |
| | | C11 OR F63 | CHROMOSOME 11 OPEN READING FRAME 63 | ENSCAFT00000018356 | CHR5_14445155-14445155_A_G | 55S>P | SUBSTITUTION | NONSYNONYMOUS CODING | CTGGGNCTAC | 18% |
| | | FIP1L1 | FIP1 LIKE 1 (S. CEREVISIAE) | ENSCAFT00000003220 | CHR13_48967897-48967897_C_ | NA | DELETION | FRAMESHIFT | AGGTANAGCAG | 40% |
| | | KRT23 | KERATIN 23 (HISTONE DEACETYLASE INDUCIBLE) | ENSCAFT00000025377 | CHR9_25094298-25094298_A_T | 389K>M | SUBSTITUTION | NONSYNONYMOUS CODING | ATCGANGTCAA | 25% |
| | | MLL3 | MYELOID/LYMPHOID OR MIXED-LINEAGE LEUKEMIA 3 | ENSCAFT00000007959 | CHR16_18937990-18937992_TGC_ | 3177QQ>Q | DELETION | IN-FRAME DELETION | GCTGTNGCTGC | 11% |
| | | MUC5AC | MUCIN 5B, OLIGOMERIC MUCUS/GEL-FORMING | ENSCAFT00000015796 | CHR18_48561759-48561759_G_A | 3305G>S | SUBSTITUTION | NONSYNONYMOUS CODING | AGACANGCCCC | 12% |
| | | NOVEL GENE | UNCHARACTERIZED PROTEIN | ENSCAFT00000036128 | CHR14_61936959-61936959_T | NA | INSERTION | FRAMESHIFT | CGGTCNCCCAG | 16% |
| | | OR52N1 | OLFACTORY RECEPTOR, FAMILY 52, SUBFAMILY N, MEMBER 1 | ENSCAFT00000010210 | CHR21_32133356-32133356_C_T | 239A>T | SUBSTITUTION | NONSYNONYMOUS CODING | GAAGGNCTTCT | 28% |

*FIG. 11 (Cont.)*

| CASE ID | TUMOR TYPE | GENE SYMBOL | GENE DESCRIPTION | TRANSCRIPT ACCESSION | NUCLEOTIDE (GENOMIC) POSITION OF MUTATION | AMINO ACID (PROTEIN) POSITION OF MUTATION | MUTATION TYPE | CONSEQUENCE | SEQUENCE CONTEXT (POSITION OF MUTATION INDICATED BY "N") | % MUTANT READS |
|---|---|---|---|---|---|---|---|---|---|---|
| | | PREX1 | PHOSPHATIDYLINOSITOL -3,4,5-TRISPHOSPHATE-DEPENDENT RAC EXCHANGE FACTOR 1 | ENSCAFT00000017540 | CHR24_38467733-38467733_C_T | 96R>H | SUBSTITUTION | NONSYNONYMOUS CODING | AGGCGNGCACA | 29% |
| | | PRPF39 | PRP39 PRE-MRNA PROCESSING FACTOR 39 HOMOLOG | ENSCAFT00000022300 | CHR8_25550886-25550886_T_ | NA | DELETION | FRAMESHIFT | GAAGANTTTGG | 24% |
| | | Q6W6S1 | UNCHARACTERIZED PROTEIN | ENSCAFT00000030697 | CHR9_50634661-50634661_A_T | 310S>T | SUBSTITUTION | NONSYNONYMOUS CODING | TTTGGNTTTAT | 27% |
| | | TENM2 | TENEURIN TRANSMEMBRANE PROTEIN 2 | ENSCAFT00000027184 | CHR4_46714792-46714792_C_T | 364R>H | SUBSTITUTION | NONSYNONYMOUS CODING | TTCGCNGGCGG | 21% |
| | | ZNF641 | ZINC FINGER PROTEIN 641 | ENSCAFT00000014313 | CHR27_9390690-9390690C_T | 363F>S | SUBSTITUTION | NONSYNONYMOUS CODING | CCCCCNCAGTG | 26% |
| 11-R04 | STS-FBS | AIDA | AXIN INTERACTOR, DORSALIZATION ASSOCIATED | ENSCAFT00000021486 | CHR3_19939874-19939874_A_G | 258F>S | SUBSTITUTION | NONSYNONYMOUS CODING | AAGCANAGCAC | 25 |
| | | BRWD3 | BROMODOMAIN AND WD REPEAT DOMAIN CONTAINING 3 | ENSCAFT00000027493 | CHRX_65189965-65189965_A_C | 275S>A | SUBSTITUTION | NONSYNONYMOUS CODING | AGTCNTGGAC | 70% |
| | | NOVEL GENE | UNCHARACTERIZED PROTEIN | ENSCAFT00000027037 | CHRX_58551749-58551749_A_G | 104K>R | SUBSTITUTION | NONSYNONYMOUS CODING | CCTGANGAATT | 17% |
| | | CAPN6 | CALPAIN 6 | ENSCAFT00000028072 | CHRX_87423838-87423838_C_T | 433B>H | SUBSTITUTION | NONSYNONYMOUS CODING | ATCTGCGGTTC | 45% |
| 16-R02 | STS-MXS | CNGB3 | CYCLIC NUCLEOTIDE-GATED CATION CHANNEL BETA-3 | ENSCAFT00000014134 | CHR29_35801978-35801978_G_A | 451R>X | SUBSTITUTION | NONSENSE | GATTCGGAAGT | 22% |
| | | NOVEL GENE | UNCHARACTERIZED PROTEIN | ENSCAFT00000035928 | CHR4_69847894-69847894_C_G | 352Y>X | SUBSTITUTION | NONSENSE | ACCTACTTTGA | 11% |
| | | PLAC8L1 | PLAC8-LIKE 1 | ENSCAFT00000010364 | CHR2_43368179-43368179_C_T | 99C>Y | SUBSTITUTION | NONSYNONYMOUS CODING | TGTCACACTCA | 20% |
| 16-R03 | STS-SCS | ANKRD11 | ANKYRIN REPEAT DOMAIN 11 | ENSCAFT00000031567 | CHR5_67220009-67220009_G_A | NA | SUBSTITUTION | SPLICE SITE DONOR | CCGTGNTGAGT | 19% |
| | | TMEM132B | TRANSMEMBRANE PROTEIN 132B | ENSCAFT00000011029 | CHR26_7467030-7467030_C_T | 198G>D | SUBSTITUTION | NONSYNONYMOUS CODING | ACAAGNCGGCC | 18% |

*FIG. 11 (Cont.)*

USE OF BACTERIA, BACTERIAL PRODUCTS, AND OTHER IMMUNOREGULATORY ENTITIES IN COMBINATION WITH ANTI-CTLA-4 AND/OR ANTI-PD-1 ANTIBODIES TO TREAT SOLID TUMOR MALIGNANCIES

CROSS-REFERENCE TO RELATED APPLICATIONS

This application is a 35 U.S.C. § 371 National Stage Entry of International Application No. PCT/US15/023633 having an international filing date of Mar. 31, 2015, which claims the benefit of U.S. Provisional Application No. 61/972,633, filed Mar. 31, 2014, and U.S. Provisional Application No. 62/035,291, filed Aug. 8, 2014, which are incorporated herein by reference in their entirety.

BACKGROUND

The prognosis for patients who present with advanced cancers of the pancreas, colon, lung, breast, ovary, brain or prostate is dismal. This tragic situation has stimulated an avalanche of research, resulting in a revolution in understanding cancer pathogenesis, significant gains in the applications of conventional chemotherapeutic agents, and some promising new agents. Unfortunately, this revolution has not yet had a major impact on the treatment of common solid tumors. Many believe that the best hope for future therapeutic gains lies in combining novel approaches with more conventional agents, such as the spores of *Clostridium novyi* (*C. novyi*), a strain of anaerobic bacteria.

The rationale for using anaerobic bacteria lies in the unique angiogenic state that exists within tumors. It is recognized that solid tumors require angiogenesis to grow, and as they grow, parts of the tumors are poorly vascularized. These avascular regions tend to have lower therapeutic drug concentrations. In addition, those drug molecules that do make it to the avascular regions usually rely on both oxygen and actively replicating cells for full potency.

It has previously been shown that a solid tumor malignancy can be treated by using some species of anaerobic bacteria. *C. novyi* is a Gram-positive, endospore-forming, obligate anaerobic bacterium. *Clostridium novyi*-NT (*C. novyi*-NT) is an attenuated form of *C. novyi* that lacks a major toxin. The use of *C. novyi*-NT has been previously reported for the treatment of cancer (Agrawal et al. (2004) *Proc. Natl. Acad. Sci. U.S.A.* 101(42):15172-15177; Bettegowda et al. (2003) *Proc. Natl. Acad. Sci. U.S.A.* 100(25): 15083-15088; Bettegowda et al. (2006) *Nat. Biotechnol.* 24(12):1573-1580; Cheong et al. (2006) *Science* 314(5803): 1308-1311; Dang et al. (2004) *Cancer Biol. Ther.* 3:326-337; Dang et al. (2004) *Proc. Natl. Acad. Sci. U.S.A.* 98(26): 15155-15160; Diaz et al. (2005) *Toxicol. Sci.* 88(2):562-575; Krick et al. (2012) *Am. J. Vet. Re.* 73(1):112-118).

Immunotherapy is also a promising approach to eradicate metastatic cancers. Recent clinical studies of neutralizing antibodies targeting two important checkpoints for T-cell mediated immunity, CTLA-4 and PD-1, have shown clinical responses in patients with solid tumor malignancies.

SUMMARY

In one aspect, the presently disclosed subject matter provides a method for treating a solid tumor in a subject, the method comprising administering to the subject a therapeutically effective amount of at least one antibody selected from the group consisting of an anti-CTLA-4 antibody and an anti-PD-1 antibody combined with at least one member of the group consisting of a bacterium, bacterial product, and an immunoregulatory entity, to treat the solid tumor. In particular aspects, the bacterium is a lethal toxin-depleted, anaerobic bacterium. In another particular aspect, the bacterial product is a component of the bacterium, for example a bacterial membrane component.

In certain aspects, the presently disclosed subject matter provides a kit for treating a solid tumor, the kit comprising at least one antibody selected from the group consisting of an anti-CTLA-4 antibody, an anti-PD-1 antibody, and at least one member of the group consisting of a bacterium, bacterial product, and an immunoregulatory entity.

In other aspects, the presently disclosed subject matter provides a method of treating cancer in a subject, the method comprising administering to the subject a therapeutically effective amount of a combination of at least one anti-CTLA-4 antibody and at least one anti-PD-1 antibody to treat the cancer.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Figure 1:
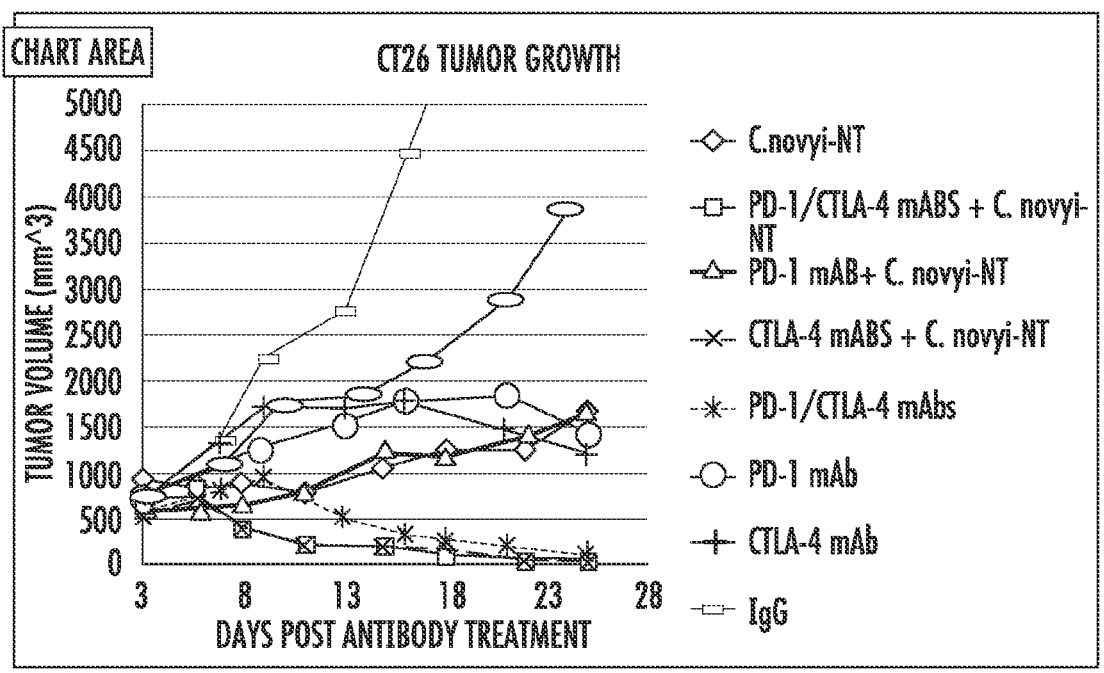
Figure 2A:
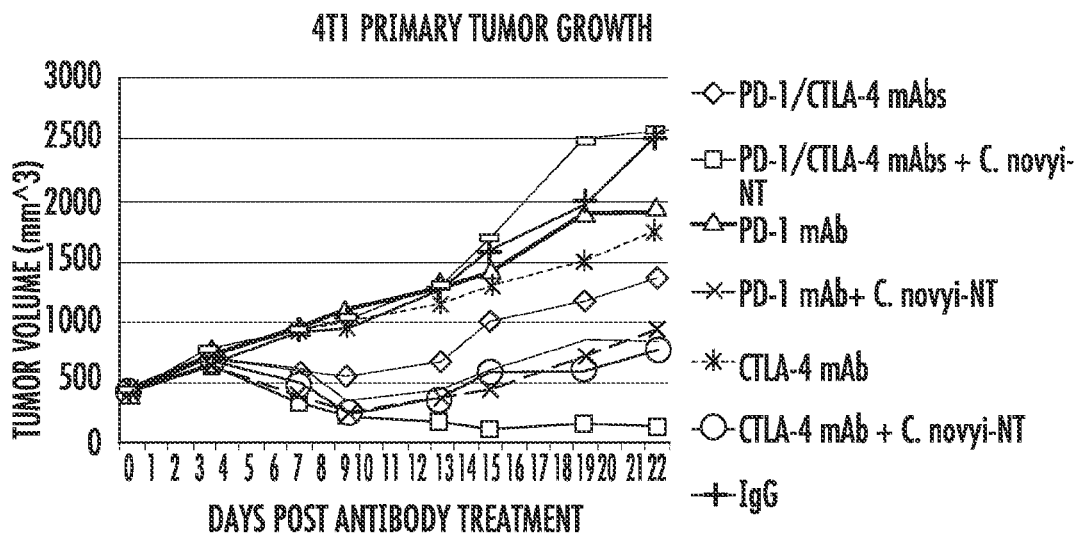
Figure 2B:
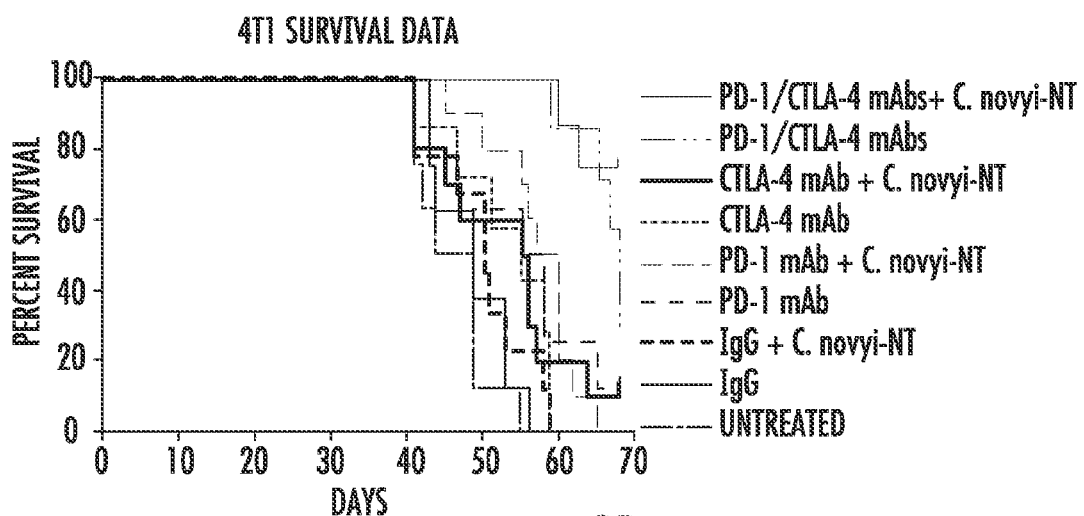
Figure 3A:
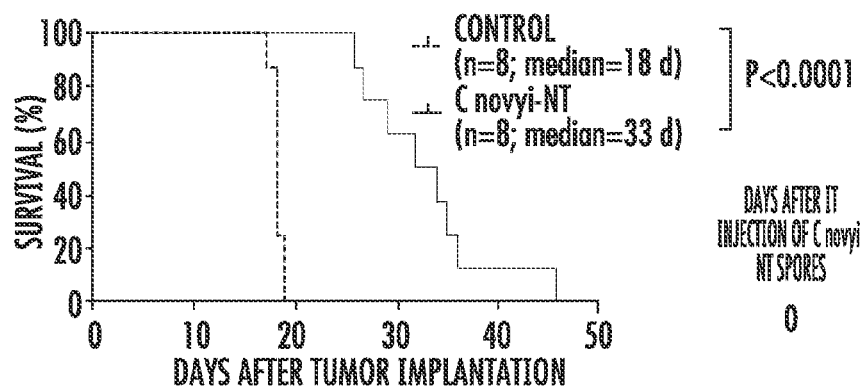
Figure 3B:
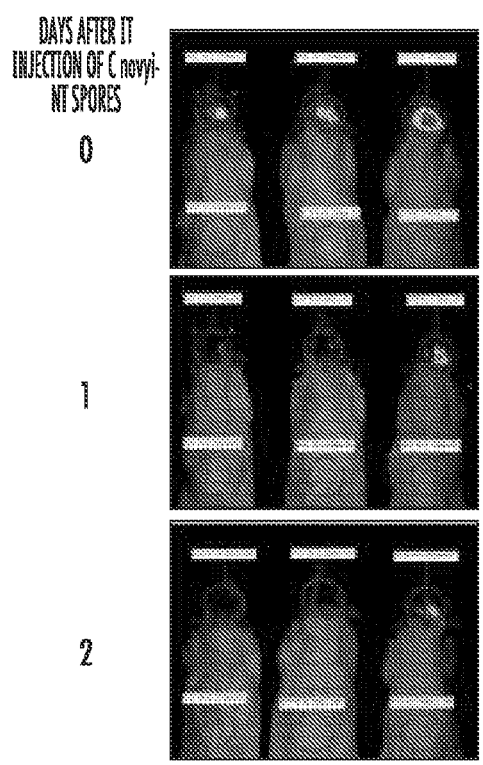
Figure 3C:
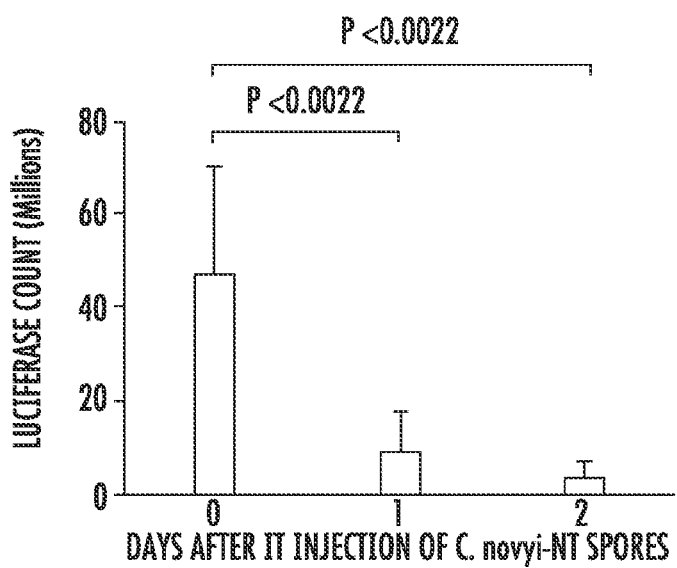
Figure 7:
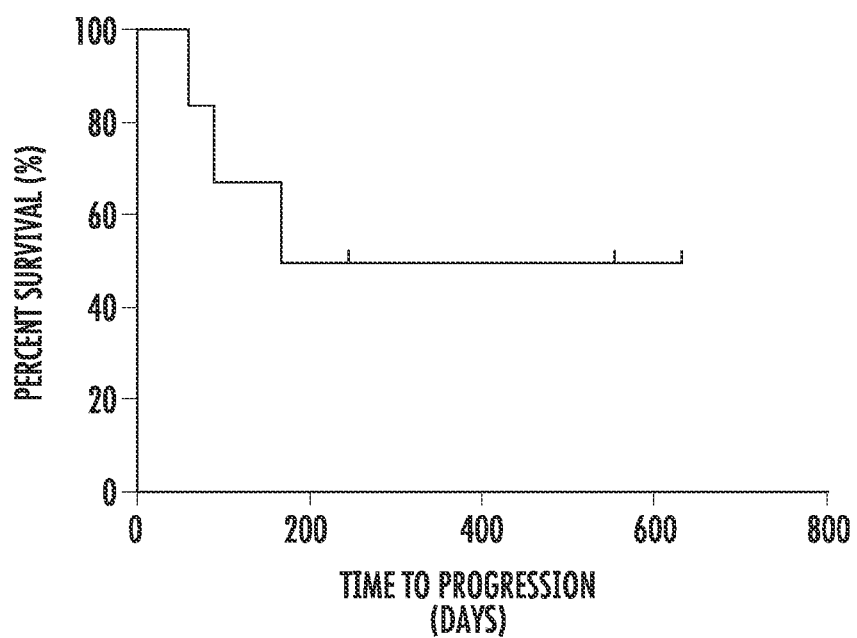

Having thus described the presently disclosed subject matter in general terms, reference will now be made to the accompanying Figures, which are not necessarily drawn to scale, and wherein:

FIG. 1 shows data from BALB/c mice bearing subcutaneous CT26 tumors treated with an anti-CTLA-4 antibody and/or anti-PD-1 antibodies with or without *C. novyi*-NT spores;

FIG. 2A and FIG. 2B show data from BALB/c mice bearing subcutaneous 4T1 tumors treated with an anti-CTLA-4 antibody and/or anti-PD-1 antibodies with or without *C. novyi*-NT spores: A) tumor growth; and B) survival data;

FIG. 3A through FIG. 3C show the response to intratumoral *C. novyi*-NT treatment in rat orthotopic brain tumor model: (A) Kaplan-Meier curves showing survival of F344 Fisher rats after orthotopic implantation of a syngeneic glioma cell line (F98). Red line, *C. novyi*-NT spores injected into tumor 12-15 days after tumor implantation; black line, control; (B) bioluminescence (Xenogen imaging system) in three representative F344 Fisher rats after orthotopic implantation of F98 glioma cell line. Images acquired on day 0 (pretreatment—day of *C. novyi*-NT spore injection), day 1 after intratumoral injection of *C. novyi*-NT spores, and day 2 after intratumoral injection of *C. novyi*-NT spores; and (C) luciferase activity (millions) on day 0 (pretreatment), day 1 after intratumoral injection of *C. novyi*-NT spores, and day 2 after intratumoral injection of *C. novyi*-NT spores;

FIG. 4A through FIG. 4D show germinated *C. novyi*-NT bacteria within microscopic rat brain tumor lesions. Gram stain showed vegetative *C. novyi*-NT bacteria (yellow arrowheads) localized in tumor (T) and stellate microinvasion (S), but not in normal brain tissue (Br) of F344 Fisher rat: (A) interface of tumor and normal brain, scale bar 30 µm; (B) interface of tumor and normal brain, scale bar 10 µm; (C) interface of normal brain, tumor, and stellate micro-invasion of neoplastic tissue, scale bar 30 µm; and (D) *C. novyi*-NT germination evident in stellate micro-invasive lesion, scale bar 10 µm;

FIG. 5A through FIG. 5F show photographic and CT images from dog 11-R01 showing a partial response to *C. novyi*-NT therapy. Images span pre-treatment to day 70 after first intratumoral dose of *C. novyi*-NT spores: (A) pre-treatment image of the peripheral nerve sheath tumor; (B) abscess formation on day 3 of the study, with extent confined to tumor; (C) medical debridement following spontaneous abscess rupture and discharge of necrotic and purulent material allowed healing by second intention; (D) the wound had healed completely by day 70 of the study, and 77.6% reduction in the largest diameter of the tumor was noted; (E) pre-treatment CT image, taken 4 days before first treatment showed extent of tumor (yellow circle) at the intersection of the pinna and cranium; and (F) post-treatment CT image on day 10 of the study showed almost complete de-bulking of tumor;

FIG. 6A through FIG. 6F show photographic and CT images from dog 04-R03 showing a complete response to *C. novyi*-NT therapy. Images span pre-treatment to day 60 after first intratumoral dose of *C. novyi*-NT spores: (A) pre-treatment image of the soft tissue sarcoma; (B) tumor localized abscess formed on day 15 of the study, one day after a third dose of *C. novyi*-NT spores; (C) tumor de-bulking was complete by day 27 of the study and healthy granulation tissue had formed; (D) the wound had healed completely by day 60 of the study, and no residual tumor was noted (complete response); (E) pre-treatment CT image, taken 5 days before first treatment, showing extent of tumor (yellow circle) on antebrachium; and (F) post-treatment CT image on day 62 of the study showing complete loss of tumor mass;

FIG. 7 shows survival analysis of dogs treated with intratumoral injection of *C. novyi*-NT. Kaplan-Meier curve showing time to progression of dogs that experienced either a complete or partial response to intratumoral injected *C. novyi*-NT. Dogs are censored if progression free at last known assessment;

FIG. 8A through FIG. 8D show CT and MRI images from the human patient: (A) post-treatment CT with contrast on day 3 demonstrating evidence of intra- and extramedullary air collection; (B) pre-treatment MRI (T1 with gadolinium contrast) of the right upper humerus showing a contrast enhancing mass involving the soft tissue and possibly adjacent bone; (C) post-treatment MRI on day 4 demonstrating diminished contrast enhancement in the tumor mass compared to baseline; and (D) post-treatment MRI on day 29 showing a homogeneous non-enhancing mass consistent with ongoing necrosis. Tumor is highlighted with yellow arrowheads;

FIG. 9A through FIG. 9D show extensive tumor necrosis in the human patient treated with *C. novyi*-NT spores: (A, B) pre-treatment tumor biopsy showing viable tumor (leiomyosarcoma) cells, scale bars 100 and 30 nm, respectively; and (C, D) post-treatment tumor biopsy, 4 days after intratumoral injection of *C. novyi*-NT spores, showing extensive necrosis of tumor cells, scale bars 100 and 30 nm, respectively;

FIG. 10 shows summary data for samples sequenced; and
FIG. 11 shows somatic alterations in canine sarcomas.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides methods and kits for treating tumors. It was hypothesized that abrogation of the negative regulations mediated through the PD-1 and CTLA-4 pathways could enhance the anticancer immune response elicited by an intratumoral bacterial infection, thus leading to cures for metastatic tumors. It has been shown herein below that by combining with an anti-CTLA-4 antibody and/or anti-PD-1 antibodies, the therapeutic effect of an antitumor bacterium is substantially enhanced. In a subcutaneous mouse tumor model, essentially 100% of the tumors were eradicated by this approach. In a metastatic tumor model, the number of metastases was markedly reduced leading to significant survival benefit. In addition, in both tumor models, combining the anti-CTLA-4 and anti-PD-1 antibodies resulted in better outcomes than using either of the antibodies alone.

Accordingly, the presently disclosed methods and kits use anti-CTLA-4 and/or anti-PD-1 antibodies in combination with bacteria, bacterial products, or other immunoregulatory entities to antagonize the negative regulatory mechanisms of the antitumor immune responses induced by the immunoregulatory entities. In addition, the presently disclosed methods and kits can be used to treat cancer by combining anti-CTLA-4 and anti-PD-1 antibodies.

I. Methods for Treating Cancer

In some embodiments, the presently disclosed subject matter provides a method for treating a solid tumor in a subject, the method comprising administering to the subject a therapeutically effective amount of at least one antibody selected from the group consisting of an anti-CTLA-4 antibody and an anti-PD-1 antibody combined with at least one member of the group consisting of a bacterium, bacterial product, and an immunoregulatory entity, to treat the solid tumor. Examples of antibodies that can be used in the presently disclosed methods include, but are not limited to, ipilimumab and tremelimumab against CTLA-4 and nivolumab against PD-1.

CTLA-4 (Cytotoxic T-Lymphocyte Antigen 4; e.g., GenBank Accession No. AAD00698.1), also known as CD152 (Cluster of Differentiation 152), is a T cell surface molecule that is a negative regulator of T cell activation. CTLA-4 was originally identified by differential screening of a murine cytolytic T cell cDNA library (Brunet et al. (1987) *Nature* 328:267-270). CTLA-4 is also a member of the immunoglobulin (Ig) superfamily and comprises a single extracellular Ig domain. CTLA-4 transcripts have been found in T cell populations having cytotoxic activity, suggesting that CTLA-4 might function in the cytolytic response (Brunet et al. (1987) *Nature* 328:267-270; Brunet et al. (1988) *Immunol. Rev.* 103-21-36). Researchers have reported the cloning and mapping of a gene for the human counterpart of CTLA-4 (Dariavach et al. (1988) *Eur. J. Immunol.* 18:1901-1905) to the same chromosomal region (2q33-34) as CD28 (Lafage-Pochitaloff et al. (1990) *Immunogenetics* 31:198-201). Sequence comparison between this human CTLA-4 DNA and that encoding CD28 proteins reveals significant homology of sequence, with the greatest degree of homology in the juxtamembrane and cytoplasmic regions (Brunet et al. (1987) *Nature* 328:267-270; Dariavach et al. (1988) *Eur. J. Immunol.* 18:1901-1905). Some studies have suggested that CTLA-4 has an analogous function as a secondary costimulator (Linsley et al. (1992) *J. Exp. Med.* 176:1595-1604; Wu et al. (1997) *J. Exp. Med.* 185:1327-1335; U.S. Pat. Nos. 5,977,318; 5,968,510; 5,885,796; and 5,885,579). However, others have reported that CTLA-4 has an opposing role as a dampener of T cell activation (Krummel (1995) *J. Exp. Med.* 182:459-465); Krummel et al. (1996) *Int'l. Immunol.* 8:519-523; Chambers et al. (1997) *Immunity* 7:885-895). It has been reported that CTLA-4 deficient mice suffer from massive lymphoproliferation (Chambers et al. (1997) *Immunity* 7:885-895). It has been reported that CTLA-4 blockade augments T cell responses in vitro (Walunas et al. (1994) *Immunity* 1:405-413) and in vivo (Kearney (1995) *J. Immunol.* 155:1032-1036), exacerbates antitumor immunity (Leach (1996) *Science* 271:1734-1736), and enhances an induced autoimmune disease (Luhder (1998) *J. Exp. Med.* 187:427-432). It has also been reported that CTLA-4 has an alternative or additional impact on the initial character of the T cell immune response (Chambers (1997) *Curr. Opin. Immunol.* 9:396-404; Bluestone (1997) *J. Immunol.* 158:1989-1993; Thompson (1997) *Immunity* 7:445-450).

PD-1 (Programmed Cell Death Protein 1; e.g. GenBank Accession No. NP_005009.2), also known as CD279 (Cluster of Differentiation 279), is a cell surface membrane protein that is expressed mainly on a subset of activated T lymphocytes, and that in humans is encoded by the PDCD1 gene (Entrez Gene GeneID: 5133; see also Ishida et al. (1992) *EMBO J.* 11:3887; Shinohara et al. (1994) *Genomics* 23:704; U.S. Pat. No. 5,698,520). PD-1 is a member of the immunoglobulin gene superfamily, has an extracellular region containing immunoglobulin superfamily domain, a transmembrane domain, and an intracellular region including an immunoreceptor tyrosine-based inhibitory motif (ITIM; Ishida et al. (1992) *EMBO J.* 11:3887; Shinohara et al. (1994) *Genomics* 23:704). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA-4 bind to B7-1 and B7-2. It has been proposed that there is a phylogenetic relationship between the MHC and B7 genes (Henry et al. (1999) *Immunol. Today* 20(6):285-8). Like CTLA-4, PD-1 is rapidly induced on the surface of T-cells in response to anti-CD3 (Agata et al. (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) *Int. Immunol.* 8:765; Nishimura et al. (1996) *Int. Immunol.* 8:773).

Two types of human PD-1 ligands have been identified: PDL1 and PDL2. PD-1 ligands comprise a signal sequence, and an IgV domain, an IgC domain, a transmembrane domain, and a short cytoplasmic tail. Both PDL1 (NCBI Reference Sequence: NP_001254635.1; Freeman et al. (2000) *J. Exp. Med.* 192:1027) and PDL2 (NCBI Reference Sequence: NP_079515.2; Latchman et al. (2001) *Nat. Immunol.* 2:261) are members of the B7 family of polypeptides. Both PDL1 and PDL2 are expressed in placenta, spleen, lymph nodes, thymus, and heart. Only PDL2 is expressed in pancreas, lung and liver while only PDL1 is expressed in fetal liver. Both PD-1 ligands are upregulated on activated monocytes and dendritic cells. The fact that PD-1 binds to PDL1 and PDL2 places PD-1 in a family of inhibitory receptors with CTLA-4.

"Functional variants" of CTLA-4 or PD-1 include functional fragments, functional mutant proteins, and/or functional fusion proteins. A functional variant of a selected polypeptide refers to an isolated and/or recombinant protein or polypeptide which has at least one property, activity and/or functional characteristic of the selected polypeptide (e.g., CTLA-4 or PD-1). As used herein, the term "activity," when used with respect to a polypeptide, e.g., CTLA-4 or PD-1, includes activities which are inherent in the structure of the wild-type protein.

For example, with respect to CTLA-4 or PD-1, the term "activity" includes the ability of CTLA-4 or PD-1 to modulate an inhibitory signal in an activated immune cell, e.g., by engaging a natural CTLA-4 or PD-1 ligand on an antigen presenting cell. PD-1 transmits an inhibitory signal to an immune cell in a manner similar to CTLA-4. Modulation of an inhibitory signal in an immune cell results in modulation of proliferation of, and/or cytokine secretion by, an immune cell. Thus, the term "CTLA-4 activity" or "PD-1 activity" includes the ability of CTLA-4 or PD-1 to bind its natural ligand(s), the ability to modulate immune cell costimulatory or inhibitory signals, and the ability to modulate the immune response.

As used herein, the term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells." As used herein, the term "costimulatory receptor" includes receptors which transmit a costimulatory signal to a immune cell. As used herein, the term "inhibitory receptors" includes receptors which transmit a negative signal to an immune cell (e.g., CTLA-4 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage.

Generally, fragments or portions of CTLA-4 or PD-1 encompassed by the presently disclosed subject matter include those having a deletion (i.e. one or more deletions) of an amino acid (i.e., one or more amino acids) relative to the wild-type CTLA-4 or PD-1 (such as N-terminal, C-terminal or internal deletions). Fragments or portions in which only contiguous amino acids have been deleted or in which non-contiguous amino acids have been deleted relative to wild-type CTLA-4 or PD-1 are also envisioned. Generally, mutants or derivatives of CTLA-4 or PD-1 encompassed by the present presently disclosed subject matter include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of CTLA-4 or PD-1 differing by the addition, deletion and/or substitution of one or more contiguous or non-contiguous amino acid residues.

Generally, a functional variant of CTLA-4 or PD-1 has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the wild-type amino acid sequence for CTLA-4 or PD-1 over the length of the variant.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) *CABIOS* 5:151-153; Higgins et al. (1992) *Comput. Appl. Biosci.* 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present presently disclosed subject matter, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen (e.g., PD-1 or CTLA-4). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (y) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); e.g., Bird et al. (1988) *Science* 242:423-426; Huston et al. (1988) *Proc. Natl. Acad Sci. USA* 85:5879-5883; and Osbourn et al. (1998) *Nature Biotechnology* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the presently disclosed subject matter bind specifically or substantially specifically to PD-1 or CTLA-4 or functional variants thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds CTLA-4 or PD-1 is substantially free of antibodies that specifically bind antigens other than CTLA-4 or PD-1. Moreover, an isolated antibody may be substantially free of other cellular material and/or chemicals.

An isolated CTLA-4 or PD-1 or functional variant thereof (or a nucleic acid encoding such polypeptides), can be used as an immunogen to generate antibodies that bind to the respective CTLA-4 or PD-1 or functional variant thereof using standard techniques for polyclonal and monoclonal antibody preparation. A full-length CTLA-4 or PD-1 can be used, or alternatively, the presently disclosed subject matter relates to antigenic peptide fragments of CTLA-4 or PD-1 ligands or functional variants thereof for use as immunogens. An antigenic peptide of a CTLA-4 or PD-1 or a functional variant thereof comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptides are regions of a CTLA-4 or PD-1 or a functional variant thereof that are located on the surface of the protein, e.g., hydrophilic regions. A standard hydrophobicity analysis of the polypeptide molecule can be performed to identify hydrophilic regions. Highly preferred epitopes encompassed by the antigenic peptides are the regions of the polypeptide molecule which are in the extracellular domain, and therefore are involved in binding. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

An immunogen comprising CTLA-4 or PD-1 or a functional variant thereof typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbant assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497; Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), a human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-PD-1 ligand monoclonal antibody (e.g., Galfre, G. et al. (1977) *Nature* 266:55052; Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present presently disclosed subject matter with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the presently disclosed subject matter are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Patent App. Pub. No. WO 92/18619; PCT Patent App. Pub. No. WO 91/17271; PCT Patent App. Pub. No. 92/20791; PCT Patent App. Pub. No. WO 92/15679; PCT Patent App. Pub. No. WO 93/01288; PCT Patent App. Pub. No. WO 92/01047; PCT Patent App. Pub. No. WO 92/09690; PCT Patent App. Pub. No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-CTLA-4 antibodies or anti-PD-1 antibodies, such as chimeric and humanized monoclonal antibodies, comprising both human and non-human portions, which can be made using standard recombinant DNA techniques, are within the scope of the presently disclosed subject matter. Such chimeric and humanized monoclonal antibodies can be produced by recombinant DNA techniques known in the art, for example using methods described in PCT Patent App. Pub. No. PCT/U586/02269; European Patent App. No. 184,187; European Patent App. No. 171,496; European Patent App. No. 173,494; PCT Application WO 86/01533; U.S. Pat. No. 4,816,567; European Patent App. No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (e.g., Carlson (1988) *Mol. Cell. Biol.* 8:2638-2646; Biocca et al. (1990) *EMBO J.* 9:101-108; Werge et al. (1990) *FEBS Lett.* 274:193-198; Carlson (1993) *Proc. Natl. Acad. Sci. USA* 90:7427-7428; Marasco et al. (1993) *Proc. Natl. Acad. Sci. USA* 90:7889-7893; Biocca et al. (1994) *Biotechnology (NY)* 12:396-399; Chen et al. (1994) *Hum. Gene Ther.* 5:595-601; Duan et al. (1994) *Proc. Natl. Acad. Sci. USA* 91:5075-5079; Chen et al. (1994) *Proc. Natl. Acad. Sci. USA* 91:5932-5936; Beerli et al. (1994) *J. Biol. Chem.* 269:23931-23936; Beerli et al. (1994) *Biochem. Biophys. Res. Commun.* 204:666-672; Mhashilkar et al. (1995) *EMBO J.* 14:1542-1551; Richardson et al. (1995) *Proc. Natl. Acad. Sci. USA* 92:3137-3141; PCT Publication No. WO 94/02610; and PCT Publication No. WO 95/03832).

Additionally, fully human antibodies could be made against CTLA-4 or PD-1 or a functional variant thereof. Fully human antibodies can be made in mice that are transgenic for human immunoglobulin genes, e.g. according to Hogan, et al., "Manipulating the Mouse Embryo: A Laboratory Manual," Cold Spring Harbor Laboratory. Briefly, transgenic mice are immunized with purified CTLA-4 or PD-1 or a functional variant thereof. Spleen cells are harvested and fused to myeloma cells to produce hybridomas. Hybridomas are selected based on their ability to produce antibodies which bind to CTLA-4 or PD-1 or a functional variant thereof. Fully human antibodies would reduce the immunogenicity of such antibodies in a human.

In one embodiment, an antibody for use in the instant presently disclosed subject matter is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to CTLA-4 or PD-1 or a functional variant thereof. In one embodiment, the bispecific antibody could specifically bind to both PD-1 ligand or a functional variant thereof and a PD-1 polypeptide or a functional variant thereof.

Yet another aspect of the presently disclosed subject matter pertains to antibodies that are obtainable by a process comprising, immunizing an animal with an immunogenic CTLA-4 or PD-1 or a functional variant thereof, or an immunogenic portion thereof unique to the CTLA-4 or PD-1, and then isolating from the animal antibodies that specifically bind to the polypeptide.

In some embodiments, the presently disclosed subject matter provides a method to treat a solid tumor using a bacterium, bacterial product, and/or other immunoregulatory entity. In other embodiments, the bacterium or bacterial product thereof is an anaerobic bacterium or bacterial product thereof. Suitable genera include but are not limited to Bifidobacteria, Lactobacilli, and Clostridia, such as *Clostridium novyi* or *Clostridium sordellii* (*C. sordellii*). In still other embodiments, the bacterium or bacterial product thereof is an obligate anaerobic bacterium or bacterial product thereof. An "anaerobic bacterium" as used herein is a bacterium that does not require oxygen for growth. An "obligate anaerobic bacterium" as used herein is a bacterium that not only does not require oxygen for growth, but is harmed by normal levels of atmospheric oxygen. In further embodiments, the anaerobic bacterium or bacterial product thereof is *Clostridium novyi* or bacterial product thereof.

In some embodiments, the bacterium or bacterial product thereof is a toxin-depleted, anaerobic bacterium or bacterial product thereof. In other embodiments, the toxin-depleted, anaerobic bacterium or bacterial product thereof is *Clostridium novyi*-NT or bacterial product thereof.

Decreasing the natural production of toxins is desirable in using bacteria therapeutically. While toxin-depleted strains need not be totally non-toxigenic, it is desirable that at least one of the toxin genes is mutated, deleted, or otherwise inactivated to render the bacteria less harmful to the subject. As used herein, the term "toxic" refers to acting as or having the effect of a poison. Preferably the toxicity is reduced by a factor of at least 2, 5, 10, 50, 100, 1000, or more. If a toxin gene is episomal or on a bacteriophage, then curing of the episome or bacteriophage can be used to delete the toxin gene. Techniques are well known in the art for mutagenesis, curing, and screening of mutants.

In some embodiments, part of or all of a toxin gene of a wild-type form of the toxin-depleted, anaerobic bacterium or bacterial product thereof is deleted to produce a "toxin-depleted" bacterium or bacterial product thereof. For example, the lethal α-toxin gene is deleted in *C. novyi*-NT. In other embodiments, the toxicity of the toxin-depleted, anaerobic bacterium is reduced by a factor of at least 2 compared to a corresponding wild-type bacterium. In still other embodiments, the toxicity of the toxin-depleted, *Clostridium novyi* is reduced by a factor of at least 2 compared to a corresponding *Clostridium novyi*. The term "wild-type" as used herein refers to the normal, non-mutated version, such as of a bacterium or a gene. The term "deletion" as used herein refers to a change in nucleotide sequence wherein one or more nucleotides are removed.

In some embodiments, the bacterial product is at least one bacterial membrane component. Bacterial membrane components may include, for example, bacterial membrane proteins attached to or associated with the membrane of *Clostridium novyi*, suitably a protein having a domain which is considered to be exposed on the outside of the bacterium and thus visible to the immune system of a human when infected with the bacteria. Reference to a bacterial membrane protein herein includes variants of naturally occurring bacterial membrane proteins such as deletion, insertion, and substitution mutations of a given bacterial membrane protein or to a protein that has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the wild-type amino acid sequence for a given bacterial membrane over the length of the variant, the variant being suitably immunogenic.

In some embodiments, other immunoregulatory entities can be combined with antibodies against CTLA-4 and/or PD-1. Such immunoregulatory entities may include, for example, immunostimulatory cytokines such as GM-CSF, Interleukin-12 (IL-12), and IL-15. Additional examples for bacterial products used for immunostimulatory purposes include inactivated bacteria or bacterial components such as Freund's complete adjuvant and Coley's toxin.

In some embodiments, at least one member of the group consisting of a bacterium, bacterial product, and an immunoregulatory entity is administered intravenously or intratumorally. In other embodiments, at least one antibody is administered by at least one method selected from the group consisting of intravenously, intramuscularly, subcutaneously, and intratumorally.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A cancer can include, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant.

In some embodiments, the presently disclosed subject matter provides a method of treating cancer in a subject, the method comprising administering to the subject a therapeutically effective amount of a combination of at least one anti-CTLA-4 antibody and at least one anti-PD-1 antibody to treat the cancer. It has been found that the combination of anti-CTLA-4 and anti-PD-1 antibodies to treat the cancer results in a better outcome than if the antibodies are administered separately. In other embodiments, the combination of anti-CTLA-4 and anti-PD-1 antibodies is administered by at least one method selected from the group consisting of intravenously, intramuscularly, subcutaneously, and intratumorally.

As used herein, the term "treating" can include reversing, alleviating, inhibiting the progression of, preventing or reducing the likelihood of the disease, disorder, or condition to which such term applies, or one or more symptoms or manifestations of such disease, disorder or condition.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

More particularly, as described herein, the presently disclosed compositions comprising at least one antibody selected from the group consisting of an anti-CTLA-4 antibody and an anti-PD-1 antibody combined with at least one member of the group consisting of a bacterium, bacterial product, and an immunoregulatory entity can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intraarticular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. The presently disclosed compositions can also be administered intratumorally, such that the compositions are directly administered into a solid tumor, such as by injection or other means.

The phrases "systemic administration," "administered systemically," "peripheral administration" and "administered peripherally" as used herein mean the administration of compositions comprising at least one antibody selected from the group consisting of an anti-CTLA-4 antibody and an anti-PD-1 antibody combined with at least one member of the group consisting of a bacterium, bacterial product, and an immunoregulatory entity, a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, drageemaking, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinaceous biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al. (1981) *J. Biomed. Mater. Res.* 15:167; Langer (1982), *Chem. Tech.* 12:98), ethylene vinyl acetate (Langer et al. (1981) *J. Biomed. Mater. Res.* 15:167), or poly-D-(−)-3-hydroxybutyric acid (EP 133,988A). Sustained release compositions also include liposomally entrapped compositions comprising at least one antibody selected from the group consisting of an anti-CTLA-4 antibody and an anti-PD-1 antibody combined with at least one member of the group consisting of a bacterium, bacterial product, and an immunoregulatory entity which can be prepared by methods known per se (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, predetermined target site, such as at a solid tumor.

In another embodiment, the presently disclosed pharmaceutical compositions may comprise PEGylated therapeutics (e.g., PEGylated antibodies or bacterial products). PEGylation is a well established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545), Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (e) improved solubility—PEG has been found to be soluble in many different solvents, ranging from water to many organic solvents such as toluene, methylene chloride, ethanol and acetone; (d) PEGylated antibody fragments can be concentrated to 200 mg/ml, and the ability to do so opens up formulation and dosing options such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by subcutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one antibody selected from the group consisting of an anti-CTLA-4 antibody and an anti-PD-1 antibody combined with at least one member of the group consisting of a bacterium, bacterial product, and an immunoregulatory entity. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions comprising at least one antibody selected from the group consisting of an anti-CTLA-4 antibody and an anti-PD-1 antibody combined with at least one member of the group consisting of a bacterium, bacterial product, and an immunoregulatory entity or vehicles include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one antibody selected from the group consisting of an anti-CTLA-4 antibody and an anti-PD-1 antibody combined with at least one member of the group consisting of a bacterium, bacterial product, and an immunoregulatory entity to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions comprising at least one antibody selected from the group consisting of an anti-CTLA-4 antibody and an anti-PD-1 antibody combined with at least one member of the group consisting of a bacterium, bacterial product, and an immunoregulatory entity are formulated into pharmaceutically acceptable dosage forms such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents, more particularly at least one antibody selected from the group consisting of an anti-CTLA-4 antibody and an anti-PD-1 antibody combined with at least one member of the group consisting of a bacterium, bacterial product, and an immunoregulatory entity. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of anti-CTLA-4 and/or anti-PD-1 antibodies in combination with bacteria, bacterial products, or other immunoregulatory entities and, optionally, additional agents can be varied so long as the beneficial effects of the combination of these agents are achieved. Accordingly, the phrase "in combination with" refers to the administration of anti-CTLA-4 and/or anti-PD-1 antibodies in combination with bacteria, bacterial products, or other immunoregulatory entities and, optionally, additional agents either simultaneously, sequentially, or a combination thereof. Therefore, a subject administered a combination of anti-CTLA-4 and/or anti-PD-1 antibodies in combination with bacteria, bacterial products, or other immunoregulatory entities and, optionally, additional agents can receive anti-CTLA-4 and/or anti-PD-1 antibodies in combination with bacteria, bacterial products, or other immunoregulatory entities and, optionally, additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the compound of anti-CTLA-4 and/or anti-PD-1 antibodies in combination with bacteria, bacterial products, or other immunoregulatory entities and, optionally, additional agents are administered simultaneously, they can be administered to the subject as separate pharmaceutical compositions, each comprising either anti-CTLA-4 and/or anti-PD-1 antibodies in combination with bacteria, bacterial products, or other immunoregulatory entities and, optionally, additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent, e.g., anti-CTLA-4 and/or anti-PD-1 antibodies in combination with bacteria, bacterial products, or other immunoregulatory entities, and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_aQ_A + Q_bQ_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

As used herein, the term "reduce" or "inhibit," and grammatical derivations thereof, refers to the ability of an agent to block, partially block, interfere, decrease, reduce or deactivate a pathway or mechanism of action. Thus, one of ordinary skill in the art would appreciate that the term "reduce" encompasses a complete and/or partial loss of activity, e.g., a loss in activity by at least 10%, in some embodiments, a loss in activity by at least 20%, 30%, 50%, 75%, 95%, 98%, and up to and including 100%.

In another aspect, the presently disclosed subject matter provides a pharmaceutical composition including anti-CTLA-4 and/or anti-PD-1 antibodies in combination with bacteria, bacterial products, or other immunoregulatory entities and, optionally, additional agents, alone or in combination with one or more additional therapeutic agents in admixture with a pharmaceutically acceptable excipient.

More particularly, the presently disclosed subject matter provides a pharmaceutical composition comprising an anti-CTLA-4 and/or anti-PD-1 antibodies in combination with bacteria, bacterial products, or other immunoregulatory entities and, optionally, additional agents and a pharmaceutically acceptable carrier.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

II. Kits for Treating Cancer

The presently disclosed subject matter also relates to kits for practicing the methods of the presently disclosed subject matter. In general, a presently disclosed kit contains some or all of the components, reagents, supplies, and the like to practice a method according to the presently disclosed subject matter. In some embodiments, the term "kit" refers to any intended any article of manufacture (e.g., a package or a container) comprising at least one antibody selected from the group consisting of an anti-CTLA-4 antibody and an anti-PD-1 antibody combined with at least one member of the group consisting of a bacterium, bacterial product, and an immunoregulatory entity and a set of particular instructions for practicing the methods of the presently disclosed subject matter. The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a subject without causing adverse reactions.

In some embodiments, the presently disclosed subject matter provides a kit for treating a solid tumor, the kit comprising at least one antibody selected from the group consisting of an anti-CTLA-4 antibody, an anti-PD-1 antibody, and at least one member of the group consisting of a bacterium, bacterial product, and an immunoregulatory entity. In other embodiments, the kit comprises a bacterium or bacterial product thereof and at least one antibody selected from the group consisting of an anti-CTLA-4 antibody and an anti-PD-1 antibody. In still other embodiments, the bacterium or the bacterial product is an anaerobic bacterium or bacterial product thereof. In further embodiments, the anaerobic bacterium or bacterial product thereof is *Clostridium novyi* or bacterial product thereof.

In some embodiments, the anaerobic bacterium or bacterial product thereof is a toxin-depleted, anaerobic bacterium or bacterial product thereof. In other embodiments, the anaerobic bacterium or bacterial product thereof is *Clostridium novyi*-NT or bacterial product thereof. In some other embodiments, part of or all of a toxin gene of a wild-type form of the toxin-depleted, anaerobic bacterium or bacterial product thereof is deleted. In further embodiments, the toxicity of the toxin-depleted, anaerobic bacterium is reduced by a factor of at least 2 compared to a corresponding wild-type bacterium. In still further embodiments, the bacterial product is at least one spore.

In some embodiments, the kit is used for treating cancer, the kit comprising a combination of anti-CTLA-4 and anti-PD-1 antibodies.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Combination Therapy in Tumor Models

Two mouse tumor models, the CT26 tumor model and the 4T1 tumor model, were used to determine the effect of CTLA-4 and PD-1 antibodies on tumors with or without the administration of *C. novyi*-NT.

Using the CT26 tumor model, BALB/c mice bearing subcutaneous CT26 tumors were treated with *C. novyi*-NT spores by intravenous injection and/or indicated antibodies by intraperitoneal injection. Animals were followed and tumor volumes determined for up to more than 3 weeks. When combined, the CTLA-4 and PD-1 antibodies were able to eradicate the immunogenic CT26 tumors with or without the administration of spores of *C. novyi*-NT, the tumor-targeting bacterial strain currently under clinical development (FIG. 1).

Using the 4T1 tumor model, BALB/c mice bearing subcutaneous 4T1 tumors were treated with *C. novyi*-NT spores by intravenous injection and/or indicated antibodies by intraperitoneal injection. Animals were followed for more than approximately 70 days. Both tumor volume (FIG. 2A) and animal survival (FIG. 2B) are shown.

In contrast to the CT26 tumor model, the 4T1 tumor is minimally immunogenic and spontaneously metastatic, making it a good model for the human disease. Cures have rarely been reported for mice bearing 4T1 tumors, especially when the tumors are larger than 200 mm$^3$. Here it was shown that neither individual antibodies nor the antibody combination were sufficient to eradicate the large primary 4T1 tumors (FIG. 2A), even though survival rate was significantly increased with the antibody combination (FIG. 2B), presumably because of improved immunologic control of micrometastases. Importantly, when spores of *C. novyi*-NT, an attenuated anaerobic tumor-targeting bacterial strain, were administered intravenously (IV) in addition to the combined antibodies, a substantial fraction of the large primary tumors were eradicated (FIG. 2A), leading to not only prolonged survival, but also cures (FIG. 2B), which is extremely rare in this tumor model.

These results suggest that remarkable clinical benefit can be expected even in minimally immunogenic tumors when a positive immunostimulation (e.g. intratumoral bacterial infection) is combined with negation of the immunologic check points (e.g. PD-1 and CTLA-4 antibodies).

Example 2

*Clostridium novyi*-NT Induces Anti-Tumor Responses

Abstract

Species of *Clostridium* bacteria are notable for their ability to lyse tumor cells growing in hypoxic environments. Here, it is shown that an attenuated strain of *Clostridium novyi* (*C. novyi*-NT) induces a microscopically precise, tumor-localized response in a rat orthotopic brain tumor model after intratumoral injection. However, it is well-known that experimental models often do not reliably predict the responses of human patients to therapeutic agents. Therefore, naturally occurring canine tumors were used as a translational bridge to human trials. Canine tumors are more like those of humans because they occur in animals with heterogeneous genetic backgrounds, are of host origin, and are due to spontaneous rather than engineered mutations. It was found that intratumoral injection of *C. novyi*-NT spores was well tolerated in companion dogs bearing spontaneous solid tumors, with the most common toxicities being the expected symptoms associated with bacterial infections. Objective responses were observed in 6 of 16 dogs (37.5%), with three complete and three partial responses. Based on these encouraging results, a human patient who had an advanced leiomyosarcoma was treated with an intratumoral injection of *C. novyi*-NT spores. This treatment resulted in a dramatic response, significantly reducing the tumor within and surrounding the bone. Taken together, these results show that *C. novyi*-NT can act as a controlled instrument to precisely eradicate neoplastic tissues, and suggest that further clinical trials of this agent in selected patients are warranted.

Introduction

Therapies that specifically target and destroy cancers must recognize differences between normal and malignant tissues (Krause and Van Etten (2005) *New Engl. J. Med.* 353:172-187; Imai and Takaoka (2006) *Nat. Rev. Cancer* 6:714-727; Sosman et al. (2012) *New Engl. J. Med.* 366:707-714; Wilson and Hay (2011) *Nat. Rev. Cancer* 11:393-410). These differences include genetic alterations and pathophysiological changes that lead to heterogeneous masses with areas of hypoxia and necrosis (Wilson and Hay (2011) *Nat. Rev. Cancer* 11:393-410; Hanahan and Weinberg (2011) *Cell* 144:646-674; Kerbel (2008) *New Engl. J. Med.* 358:2039-2049; Chung and Ferrara (2011) *Annu. Rev. Cell Dev. Bio.* 27:563-584; Baish et al. (2011) *Proc. Natl. Acad. Sci. USA* 108:1799-1803). Systemically delivered anti-cancer agents rely on tumor vasculature for delivery and as such, are less effective in poorly vascularized, hypoxic tumor regions (Wilson and Hay (2011) *Nat. Rev. Cancer* 11:393-410). Additionally, radiotherapy fails to kill hypoxic cells because oxygen is a required effector of radiation-induced cell death (Horsman et al. (2012) *Nat. Rev. Clin. Oncol.* 9:674-687). For these key reasons, non-resectable, locally-advanced tumors are particularly difficult to manage with conventional therapies.

Tumors are composed of necrotic, hypoxic, and well-oxygenated regions. Hypoxic tumor regions are more resistant to systemic anti-cancer agents and radiotherapy. However, they provide a fertile ground for the growth of anaerobic bacteria. Therefore, the hypoxic areas of tumors offer a perfect niche for the growth of anaerobic bacteria. In principle, this offers an opportunity for eradication of advanced local tumors in a precise manner, sparing surrounding well-vascularized normoxic tissue. Since Coley's original work treating cancer patients with *Strepococcus pyogenes* over 100 years ago, a variety of anaerobic bacteria have been considered for this purpose (Coley (1910) *Proc. Roy. Soc. Med.* 3:1-48; Coley (1991) *Clin. Orthop. Relat. Res.* 3-11). This early work failed to produce a viable anti-cancer agent due in part to poor reproducibility and unacceptable toxicity. More recent work involved attenuated strains of *Salmonella typhimurium*, and others (Forbes (2010) *Nat. Rev. Cancer* 10:785-794; Wei et al. (2008) *Cancer Lett.* 259:16-27). However, whereas Phase I clinical trials of *S. typhimurium* in both dogs and human patients demonstrated that the bacterium could be safely administered and targeted to tumor, limited efficacy was observed (Toso et al. (2002) *J. Clin. Oncol.* 20:142-152; Thamm et al. (2005) *Clin. Cancer Res.* 11:4827-4834). In an effort to augment efficacy with *S. typhimurium* therapy, genetically modified strains incorporating cytosine deaminase, that convert systemically administered 5-fluorocytosine to 5-flurouracil, have been developed and evaluated in patients (Nemunaitis et al. (2003) *Cancer Gene Ther.* 10:737-744).

One particularly promising bacterium, however, is *Clostridium novyi* (Dang et al. (2001) *Proc. Natl. Acad. Sci. USA* 98:15155-15160). *C. novyi* is a highly mobile, spore-forming bacterium that is exquisitely sensitive to oxygen. A derivative of the wild-type strain, called *C. novyi*-NT, was generated through removal of the α-toxin gene (Dang et al. (2004) *Cancer Bio. Ther.* 3:326-337; Dang et al. (2001) *Proc. Natl. Acad. Sci. USA* 98:15155-15160). A single dose of intravenously injected *C. novyi*-NT spores into mice and rabbits bearing transplanted syngeneic tumors led to localized tumor necrosis, intense inflammatory responses, and complete responses in 25-30% of the treated animals (Agrawal et al. (2004) *Proc. Natl. Acad. Sci. USA* 101: 15172-15177). On the basis of these data, intravenously injected *C. novyi*-NT spores were evaluated in spontaneously occurring canine tumors (Krick et al. (2012) *Amer. J. Vet. Res.* 73:112-118). However, at doses that exhibited acceptable toxicity, no complete responses were observed.

Given the remarkable ability of intravenously injected *C. novyi*-NT spores to localize, germinate within, and destroy murine tumors while leaving surrounding normal tissues intact, it was hypothesized that direct intratumoral injection of spores into solid tumors might have advantages over administration via the intravenous route. One problem encountered with systemic injection of spores is the small proportion of spores that actually are delivered to tumors (Diaz et al. (2005) *Toxicol. Sci.* 88:562-575). This problem is compounded in large animals and human patients, which have relatively large blood volumes and relatively small tumors compared to mice. With intratumoral injection, orders of magnitude more spores can be directly deposited within the target tumor, to overcome this problem. Additionally, intratumoral injection of spores may also have advantages over other conventional forms of local therapy, such as surgery and radiotherapy. Theoretically, *C. novyi*-NT therapy could result in the precise, microscopic excision of neoplastic cells from tumors without the need to excise a margin of normal tissue. Intratumoral injection of *C. novyi*-NT spores could also elicit a potent localized inflammatory response as well as an adaptive immune response against tumor cells (Agrawal et al. (2004) *Proc. Natl. Acad. Sci. USA* 101:15172-15177). Based on this reasoning, the safety and efficacy of intratumorally injected *C. novyi*-NT spores was investigated in a preclinical animal model as well as in a comparative study of dogs with spontaneously occurring cancers. The first-in-human data from a patient treated with intratumorally injected *C. novyi*-NT spores is also reported.

Materials and Methods

Study Design:

The preclinical, proof-of-concept study was conducted using the rat orthotopic F98 glioma model to demonstrate *C. novyi*-NT-induced infection specifically and precisely localized in the tumor lesions. Luciferase activity and Kaplan-Meier survival curves were used to assess therapeutic benefit. A comparative study in companion dogs with spontaneous solid tumors was used to bridge translation between preclinical and human studies. The experimental unit was one study dog and each dog received up to four cycles of treatment. Placebo control, blinding, or randomization was not used in the study. Formal a priori statistical hypotheses were not planned for this comparative study. Descriptive summary statistics and analysis were provided post-hoc. The human clinical trial is an ongoing open-label, non-randomized, multi-center Phase I study with a standard "3+3" dose escalation. The study was designed to: (i) determine the safety profile, dose limiting toxicities, and maximum tolerated dose of *C. novyi*-NT spores in humans with treatment-refractory solid tumor malignancies when administered as a single intratumoral injection, (ii) document preliminary anti-tumor activity of both the injected tumor and overall response, (iii) study the disposition of circulating *C. novyi*-NT spores, and (iv) measure the host immune and inflammatory responses associated with *C. novyi*-NT treatment.

Cell Lines and Tissue Culture:

Rat F98 glioma cell line transfected with luciferase construct via lentivirus was maintained in Dulbecco's Modified Eagle Medium (DMEM) supplemented with 10% fetal bovine serum (FBS) and 1% penicillin and streptomycin.

Rat Orthotopic Brain Tumor Model:

All animal experiments involving rats were approved by the Johns Hopkins University Institutional Animal Care and Use Committee. Six week old female F344 Fisher rats (weight 100-150 gram) were purchased from the National Cancer Institute. For the implantation procedure, female F344 Fisher rats were anesthetized via intraperitoneal injection of ketamine hydrochloride (75 mg/kg; 100 mg/mL ketamine HCl; Abbot Laboratories), xylazine (7.5 mg/kg; 100 mg/mL Xyla-ject; Phoenix Pharmaceutical, Burlingame, CA), and ethanol (14.25%) in a sterile NaCl (0.9%) solution. F98 glioma cells ($2\times10^4$) transfected with a luciferase construct via lentivirus were stereotactically implanted through a burr hole into the right frontal lobe located 3 mm lateral and 2 mm anterior to the bregma, as described before (Bai et al. (2011) *Neuro-oncology* 13:974-982). Tumor size was assessed via Xenogen instrument with intraperitoneal injection of 8 mg/rat D-luciferin potassium salt at day 12 after implantation of the tumor cells. Subsequently, 3 million *C. novyi*-NT spores, produced as previously described (Dang et al. (2004) *Proc. Natl. Acad. Sci. U.S.A.* 98(26): 15155-15160; Bettegowda et al. (2006) *Nat. Biotechnol.* 24:1573-1580), were stereotactically injected into the intracranial tumor using the same coordinates as described above. The rats were treated with 10 mg/kg/day of intraperitoneal dexamethasone for the first 2 days to minimize the risk of post-operative edema; this closely mimics the standard clinical protocol used in human patients after brain tumor surgery and biopsy. Control rats were stereotactically injected with the same volume of PBS and treated with 10 mg/kg/day of intraperitoneal dexamethasone for the first 2 days Animals were observed daily for any signs of deterioration, lethargy, neurotoxicity, or pain in accordance with the Johns Hopkins Animal Care and Use Guidelines. If symptoms of distress were present, supportive therapy with hydration and doxycycline (loading dose of 15 mg/kg intraperitoneal followed by 10 mg/kg every 12 hours as maintenance) was initiated and continued for a 7 day period. If symptoms persisted and/or resulted in debilitation, moribund animals were euthanized. The effectiveness of intratumorally injected *C. novyi*-NT spores was evaluated by Kaplan-Meier survival curves, as well as remaining tumor burden on brain sections. For the latter, brains were collected post-mortem, placed in formaldehyde, and embedded in paraffin for additional pathological studies. Gram-stained slides, counter-stained with safranin, and H&E-slides were obtained according to standard procedure guidelines.

Statistical Analyses:

Kaplan-Meier survival curves and luciferase count graphs were created and analyzed with a Mantel-Cox and Mann-Whitney tests, respectively, using GraphPad Prism v.5.00 (GraphPad Software, San Diego, CA).

Genomic DNA Isolation for Sequencing:

Genomic DNA from dogs participating in the comparative study of intratumorally injected *C. novyi*-NT spores was extracted from peripheral blood lymphocytes (PBLs) and formalin-fixed, paraffin-embedded tumor tissue using the QIAamp DNA mini kit (QIAGEN, Valencia, CA) according to the manufacturer's protocol.

Sequencing and Bioinformatic Analysis:

Genomic purification, library construction, exome capture, next generation sequencing, and bioinformatic analyses of tumor and normal samples were performed at Personal Genome Diagnostics (PGDx, Baltimore, MD). In brief, genomic DNA from tumor and normal samples were fragmented and used for Illumina TruSeq library construction (Illumina, San Diego, CA). The exomic regions were captured in solution using the Agilent Canine All Exon kit according to the manufacturer's instructions (Agilent, Santa Clara, CA). Paired-end sequencing, resulting in 100 bases from each end of the fragments, was performed using a HiSeq 2000 Genome Analyzer (Illumina, San Diego, CA). The tags were aligned to the canine reference sequence (CanFam2.0) using the Eland algorithm of CASAVA 1.7 software (Illumina, San Diego, CA). The chastity filter of the BaseCall software of Illumina was used to select sequence reads for subsequent analysis. The ELAND algorithm of CASAVA 1.7 software (Illumina, San Diego, CA) was then applied to identify point mutations and small insertions and deletions. Known polymorphisms recorded in dbSNP131 (CanFam2.0) were removed from the analysis. Potential somatic mutations were filtered and visually inspected as described previously (Jones et al. (2010) *Science* 330:228-231).

Preparation and Intratumoral Injection of *C. novyi*-NT Spores in Spontaneous Canine Tumors:

*C. novyi*-NT spores for use in the comparative canine study were produced as previously described (Dang et al. (2004) *Proc. Natl. Acad. Sci. U.S.A.* 98(26):15155-15160; Bettegowda et al. (2006) *Nat. Biotechnol.* 24:1573-1580). In brief, bacteria were cultured in sporulation medium for at least two weeks to ensure maximum yield of mature spores. Mature spores were purified through two consecutive, continuous Percoll gradients followed by four washes and re-suspensions in PBS. Sterility testing of the final product was performed by culturing product in Soybean-Casein Digest Medium and Thioglycollate Medium in accordance with FDA 21CFR610.12 guidelines (Nelson Laboratories, Salt Lake City, UT). Germination efficiency assays were performed under anaerobic conditions on *Brucella agar* with 5% horse blood to ensure the spores meet preset viability criteria. Spores were packaged in sterile 1.8 mL cryovials with O-ring sealed screw caps (Simport, Beloeil, Canada) at a volume of 1000 µL and a concentration of $1 \times 10^9$ spores/mL. *C. novyi*-NT cryovials were stored at 2-8° C. For dosing, a 0.4 mL aliquot of the stock spore solution was packaged into 0.5 mL cryovials. After dosing, the cryovials and unused *C. novyi*-NT spores were discarded according to applicable regulations for disposal of Biosafety Level 2 material.

Prior to intratumoral injection, spores were re-suspended with a vortex, mixing at maximum speed for 10 seconds for a total of three times before being withdrawn into a 1 mL syringe. The injection site was aseptically prepared. If available, ultrasound or computed tomography (CT) was used to identify a necrotic region of the tumor. If a necrotic region was not identified, the injection was directed to the center of the tumor. The needle was inserted once into the pre-defined region and 100 µL of spore suspension ($1 \times 10^8$ *C. novyi*-NT spores) were dispensed with even pressure. The injection needle was removed slowly and the injection site sterilized.

Design and Conduct of Comparative Canine Study:

All animal research involving dogs was performed in compliance with applicable local, state, national, and international animal welfare regulations, and adhered to the highest standards of animal care and use. Written, informed consent was obtained from the owner prior to enrollment of each dog. The study protocol and informed consent were approved by the Animal Clinical Investigation (ACI, Washington, DC) Animal Care and Use Committee to ensure the ethical care of dogs enrolled in the study.

Client-owned dogs with spontaneous tumors received up to four cycles of intratumoral *C. novyi*-NT spores. A cycle consisted of one intratumoral injection of $1 \times 10^8$ *C. novyi*-NT spores (in 100 µL PBS) into one target tumor. Cycles of intratumoral *C. novyi*-NT spores were typically one week apart. No placebo control or masking was used. Dogs were followed for 90 days and extended follow-up for disease progression and survival were warranted when available. Early withdrawal from the study was allowed for toxicity or progressive disease.

Dogs were enrolled at multiple sites participating in the Animal Clinical Investigation oncology network (ACI, Washington, DC). Treatment, management, and study evaluations were overseen by board-certified veterinary oncologists. Enrollment was offered to client-owned dogs with spontaneous solid tumors, with a preference for soft-tissue sarcomas that had failed standard therapy or whose owner(s) had declined such therapy. Participation was restricted to tumor bearing dogs with a target lesion having a longest diameter between 1 and 7 centimeters. Dogs with tumors located in areas where abscess development would be catastrophic (e.g., nasal tumors that extended into the brain or significant pulmonary metastatic disease) were excluded from the study. Dogs with evidence of an active bacterial infection requiring systemic antibiotic therapy within seven days or cancer therapy (chemotherapy, radiation therapy, and immunotherapy) within 21 days of *C. novyi*-NT spore treatment were ineligible. Dogs were required to have a performance score of 0 or 1 (Table 1) and to be available for the full duration of the study for enrollment. Concurrent use of anticancer agents and participation in other clinical trials were prohibited.

Dogs were hospitalized for four days after the first intratumoral injection of *C. novyi*-NT, and for 24-48 hours after subsequent intratumoral injections for observation at the discretion of the investigator. Intravenous fluid therapy was administered after each intratumoral injection of *C. novyi*-NT spores for two hours at a rate of 4 mL/kg/hr. Subcutaneous fluid therapy was administered for four days after each intratumoral injection of *C. novyi*-NT spores at a rate of 20 mL/kg/day. Dogs were closely monitored for six hours after each intratumoral injection of *C. novyi*-NT spores.

Study evaluations were undertaken as described in Table 2. Pre-screening evaluations were conducted 1 to 14 days before the first cycle of intratumoral *C. novyi*-NT spores. Dogs were monitored periodically on both an inpatient and outpatient basis during the study. Laboratory samples were taken as defined in Table 2 and included a complete blood count, serum biochemistry, prothrombin time, partial thromboplastin time, and urinalysis. Imaging was performed at screening and included regional CT, thoracic radiography, and abdominal ultrasonography. Additional imaging was conducted during the study at the investigator's discretion.

Adverse events were evaluated, where possible, using the Veterinary Co-operative Oncology Group—Common Terminology Criteria for Adverse Events (VCOG-CTCAE) v1.0 (Veterinary co-operative oncology group (2004) *Vet. Comp. Oncol.* 2:195-213), with terminology from the Veterinary Dictionary for Drug Related Affairs (VeDDRA) rev.4 (European Medicines Agency (2012) *Combined VeDDRA list of clinical terms for reporting suspected adverse reactions in animals and humans to veterinary medicinal products*). Terminologies for adverse events related to *C. novyi*-NT germination (target lesion reactions) are defined in Table 3. Clinical observations without appropriate VeDDRA or target lesion reaction terminology were classified separately as uncoded signs (Table 4). Relationship to *C. novyi*-NT therapy was determined by the reporting investigator.

Longest diameter tumor measurements of the target (injected) lesion were made on day 0, day 7, day 14, day 21, day 60 and day 90 post-treatment (Table 2). Non-target and new lesions were recorded but not measured. The best overall target response was evaluated on or after the day 21 study visit: complete response (CR) was defined as the complete disappearance of the target lesion; partial response (PR) was defined as at least a 30% decrease in the longest diameter of the target lesion; and progressive target disease (PD) was defined as at least a 20% increase in the longest diameter of the target lesion or the appearance of new non-target lesions. Stable disease (SD) was defined as insufficient decrease or increase in the longest diameter of the target lesion to qualify as CR, PR, or PD. In the case of *C. novyi*-NT related abscesses, medical, or surgical debridement of necrotic tissue was at the discretion of the investigator.

Evaluation of surgical samples and necropsies were conducted by board certified veterinary pathologists. Tissue specimens were fixed in 10% neutral buffered formalin and embedded in paraffin. Slides stained with H&E and or gram stained slides were prepared for evaluation according to standard procedure guidelines. For immunohistochemistry (IHC), formalin-fixed, paraffin-embedded tumor tissue was sectioned at 5 µm, deparaffinized in xylene, and rehydrated through graded alcohols. Antigen retrieval was done by heating slides in unmasking solution for 10 minutes (catalog no. H-3300, Vector Laboratories, Burlingame, CA). All slides were then incubated in 10 percent blocking serum from the animal species from which the secondary antibody was made, in PBS for 10 minutes at room temperature. Primary antibodies S100 (catalog no. Z0311, DAKO, Carpinteria, CA) and anti-smooth muscle actin (catalog no. M0851, DAKO, Carpinteria, CA) were used at 1:100 for 60 minutes at room temperature (Duke et al. (2014) *Vet. Pathol.*; Zarfoss et al. (2007) *Vet. Pathol.* 44:276-284). Secondary antibodies (catalog no. BA-1000 and BA-2000, Vector Laboratories, Burlingame, CA) labeled with DAB were used at 1:500 for 30 minutes at room temperature. Sections were incubated with ABC reagent (Vector Laboratories, Burlingame, CA) and counterstained with hematoxylin. Tumor grades were assigned to each based on published criteria (Dennis et al. (2011) *Vet. Pathol.* 48:73-84; Patnaik et al. (1984) *Vet. Pathol.* 21:469-474; Smedley et al. (2011) *Vet. Pathol.* 48:54-72; Sabattini et al. (2014) *Vet. Pathol.*).

Phase I Human Clinical Trial of Intratumorally Injected *C. novyi*-NT Spores:

An open-label, non-randomized, multi-center Phase I safety study of a single intratumoral injection of *C. novyi*-NT spores is currently ongoing in patients with treatment-refractory solid tumors.

The clinical study protocol was reviewed and approved by the Institutional Review Board (IRB) of each participating institution, and all regulatory steps were performed under the guidance of the Food and Drug Administration (FDA) (clinicaltrials.gov; NCT01924689). All patients were required to sign a written Informed Consent Form (ICF) before inclusion in the study.

The primary objectives of this Phase I study is to determine the safety profile, dose limiting toxicities, and maximum tolerated dose of intratumorally injected *C. novyi*-NT. In addition, the anti-tumor activity of intratumoral *C. novyi*-NT was explored.

Preparation and Intratumoral Injection of *C. novyi*-NT Spores in the Phase I Study:

*C. novyi*-NT spores were manufactured and formulated by Omnia Biologics, Inc. (Rockville, MD). The clinical supply of *C. novyi*-NT spores was packaged in a single-use 2 mL sterile and pyrogen-free, Type I borosilicate glass vial with a rubber stopper and aluminum seal with a tamper resistant cap at a concentration of $8.52 \times 10^8$ spores/mL suspended in 1.0 mL of sterile phosphate buffered saline (PBS). Vials were stored between 2-8° C. in a controlled temperature environment under constant temperature monitoring.

After a patient was enrolled in the trial, one vial was shipped to the study site. Further preparation of *C. novyi*-NT was required and occurred on the same day of the intratumoral injection. Dilution of the concentrated spore suspension was performed in a designated biological safety cabinet using sterile saline (0.9%) infusion bags of appropriate size to achieve the required dose based on the assigned cohort. The injection volume (3 mL) was then withdrawn from the saline bag and injected under radiographic guidance. *C. novyi*-NT spores were injected with an 18-gauge multi-pronged needle (Quadra-Fuse®, Rex-Medical, Conshohocken, PA).

Design and Conduct of Human Clinical Trial:

The study was conducted with a standard 3+3 dose-escalation design. To enroll on the study, patients must have been diagnosed with an advanced solid tumor malignancy, with a target tumor that was palpable and clearly identifiable under ultrasound or radiographic guidance. In addition, the target lesion must have had a longest diameter ≥1 cm, have been measurable as defined by RECIST 1.1 criteria, and have been amenable to percutaneous injection of *C. novyi*-NT spores.

The eligibility criteria included: a history of a treatment refractory solid tumor malignancy; at least 18 years of age; an Eastern Cooperative Oncology Group (ECOG) performance status ≤2; an ability to stay within 45 minutes of an emergency room and having a caregiver for 28 days after intratumoral injection. The exclusion criteria included: pregnancy; a primary brain malignancy or brain metastases; clinically significant ascites or clinical evidence or history of portosystemic hypertension or cirrhosis; a Glasgow Coma Score (GCS) <15; a serum creatinine level >1.5× the upper limit of normal (ULN), chronic renal failure that required hemodialysis or peritoneal dialysis; an oxygen saturation (SpO2) <95% (room air); a mean arterial blood pressure (BP) <70 mmHg; a platelet count ≤100,000/mm3; a hemoglobin <9.0 g/dL; an absolute neutrophil count (ANC) <1,000/mm3; clinically significant pleural effusion, pericardial effusion, circumferential pericardial effusion, or any effusion that was greater than 1.0 cm at any location around the heart; a need for ongoing treatment with an immunosuppressive agent; a history of solid organ transplantation; systemic or localized infection.

Eligible patients were admitted and enrolled into a dose cohort. Patients remained hospitalized after *C. novyi*-NT spore injection and were observed for 8 days. Patients returned to the clinical site for routinely scheduled follow-up visits, during which time assessments of safety and efficacy were performed.

Clinical response and progression was evaluated using RECIST version 1.1. Objective responses were measured by serial CT or MRI scans of the injected tumor, as well as distant metastases (up to 5 lesions).

Public Health Implications of *C. novyi*-NT Therapy:

*C. novyi* is a spore-forming, gram-positive, obligate anaerobe commonly found in soil (Nishida and Nakagawara (1964) *J. Bacteriol.* 88:1636-1640). *C. novyi*-NT was derived from a strain of *C. novyi* by deleting a toxin gene necessary for systemic pathogenicity (Dang et al. (2004) *Proc. Natl. Acad. Sci. U.S.A.* 98(26):15155-15160). Extensive preclinical evaluation of *C. novyi*-NT has failed to demonstrate germination of *C. novyi*-NT spores in non-tumor tissue (Diaz et al. (2005) *Toxicol. Sci.* 88:562-575). In addition, while *C. novyi*-NT spores are resistant to oxygen, vegetative *C. novyi*-NT is highly sensitive to oxygen (Diaz et al. (2005) *Toxicol. Sci.* 88:562-575). As such, vegetative *C. novyi*-NT is not viable outside the hypoxic tumor microenvironment. Although the risk to health of the public with *C. novyi*-NT therapy is thought to be minimal, precautions for the handling of *C. novyi*-NT and disposal of *C. novyi*-NT contaminated material were instigated. For the canine comparative study: protective gloves were worn when handling feces, urine, saliva, or tumor discharge from treated dogs; stool was placed into a sealed plastic bag and disposed with general household waste; items soiled with urine, stool, or tumor discharge were washed separately from other laundry. For the human clinical study, standard protective gowns and gloves were required for healthcare providers.

Results

Figure 4A:
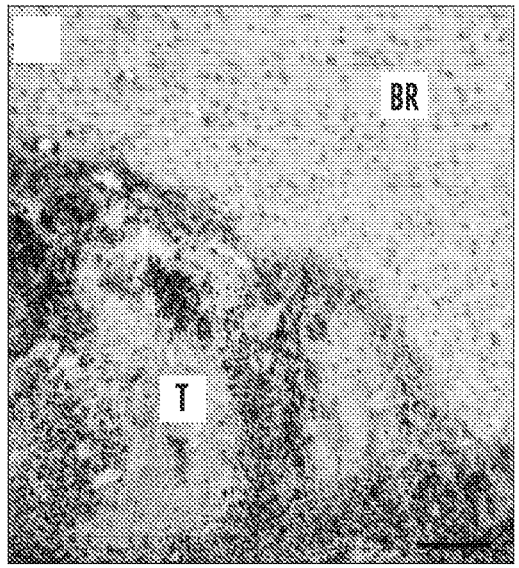
Figure 4B:
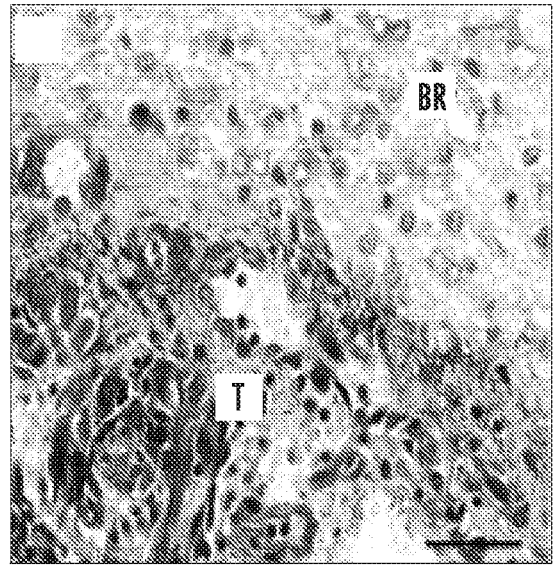
Figure 4C:
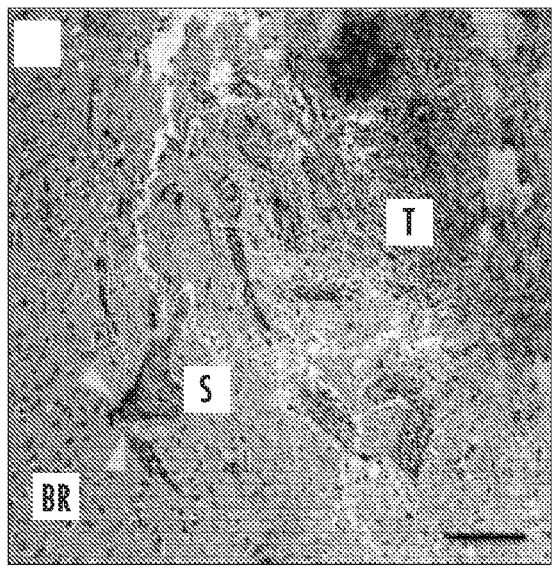
Figure 4D:
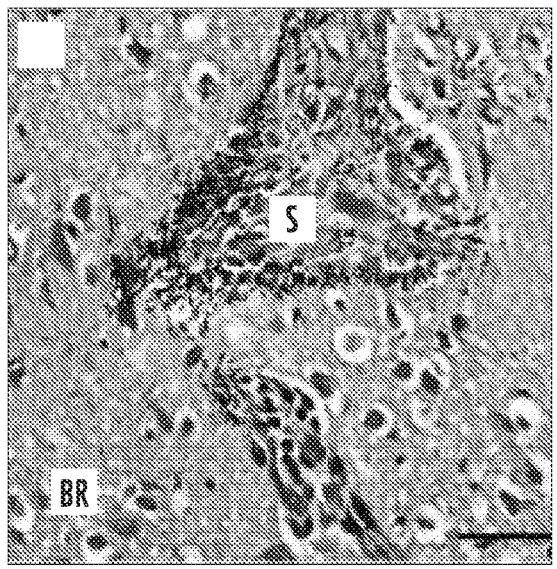
Figure 5A:
Figure 5B:
Figure 5C:
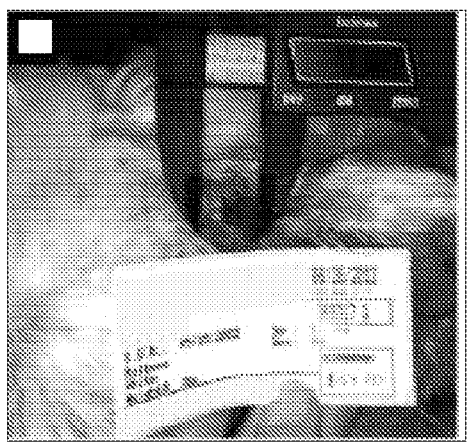
Figure 5D:
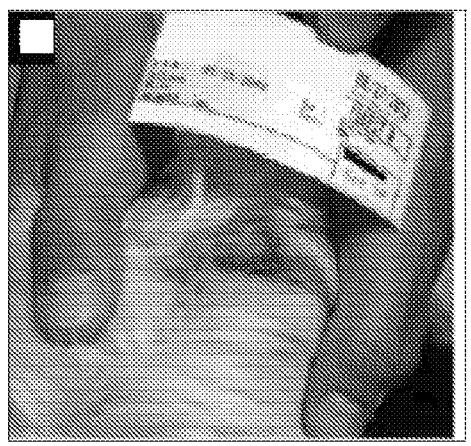
Figure 5E:
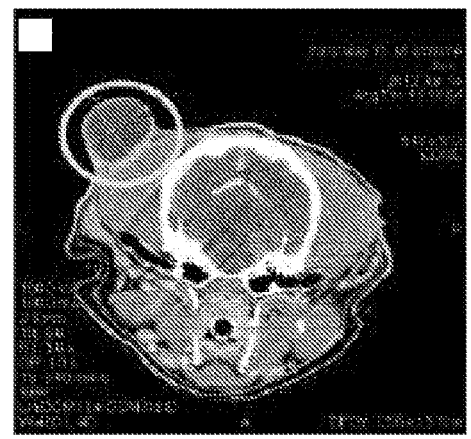
Figure 5F:
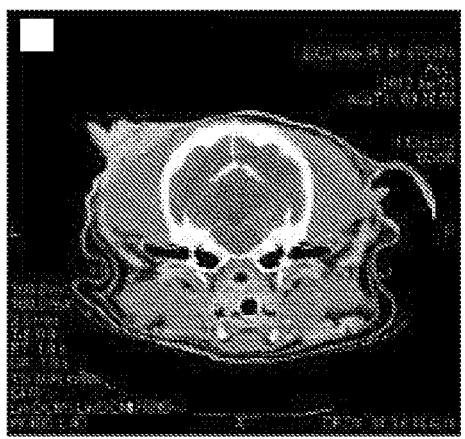

Intratumorally-Injected *C. novyi*-NT Spores Specifically Target Tumor Tissue and Prolong Survival in Rats:

High grade gliomas exhibit notable histopathological variability, with extensive regions of hypoxia and necrosis. Though this tumor type generally does not metastasize, its complexity along with the sheltered location within the central nervous system has made this cancer one of the most difficult to treat. Complete surgical excision is nearly always impossible due to anatomical restrictions and the infiltrative growth pattern leading inexorably to tumor recurrences. Gliomas, therefore, seemed to represent a tumor type for which local injection of *C. novyi*-NT spores could be therapeutically useful. To evaluate this possibility, F98 rat glioma cells engineered to express luciferase were orthotopically implanted into 6-week old F344 Fisher rats, resulting in locally invasive tumors that were rapidly fatal (FIG. 3A). Stereotactic intratumoral injection of *C. novyi*-NT spores into the tumors of these rats resulted in their germination within 24 hours and a rapid fall in luciferase activity, an indicator of tumor burden, within 48 hours (FIGS. 3B and 3C). *C. novyi*-NT germination was demonstrated by the appearance of vegetative forms of the bacterium. Strikingly, *C. novyi*-NT precisely localized to the tumor, sparing adjacent normal cells only a few microns away (FIGS. 4A and 4B). Moreover, these vegetative bacteria could be seen to specifically grow within and concomitantly destroy islands of micro-invasive tumor cells buried within the normal brain parenchyma (FIGS. 4C and 4D). This bacterial treatment led to a significant survival advantage in this extremely aggressive rat model (FIG. 3A, P-value <0.0001). Brain edema as a result of *C. novyi*-NT germination was common and medically managed. Abscess formation in the brain was not clearly observed in the syngeneic rat model with appropriate use of antibiotics. Abscess formation, however, is a potential side effect of the therapy, which could develop in human patients and would necessitate neurosurgical abscess excision and drainage, a routine clinical procedure. Regardless, given the dismal prognosis of high-grade gliomas, the benefits of *C. novyi*-NT treatment might outweigh associated potential risks.

Canine Soft Tissue Sarcomas Resemble Human Tumors:

Preclinical animal studies of anticancer agents often do not recapitulate the observed effects in people. In companion dogs, however, clinically used therapeutic agents induce similar toxicities and effects as found in people (Paoloni and Khanna (2008) *Nat. Rev. Cancer* 8:147-156). Studies of investigational therapies in companion dogs can represent a crucial bridge between preclinical animal studies and human clinical studies. In particular, canine soft tissue sarcomas are an excellent model as they are common in many breeds of dogs and have clinical and histopathological features remarkably similar to those of human soft tissue sarcomas (Paoloni and Khanna (2008) *Nat. Rev. Cancer* 8:147-156; Vail and MacEwen (2000) *Cancer Invest.* 18:781-792). In addition, the superficial location of many soft tissue sarcomas allows for rapid assessment and management of therapy-related abscess formation.

Recent advances in genomics have expanded knowledge of cancer genetics in people and led to recent evidence of a link between mutational burden, tumor immunogenicity and response to immunotherapies such as anti-PD-1 and anti-PD-L1 antibodies (Champiat et al. (2014) *Oncoimmunology* 3:e27817). However, comparatively little is known about the genetic landscape of canine cancers. As *C. novyi*-NT has been shown to induce a potent anti-tumor immune response (Agrawal et al. (2004) *Proc. Natl. Acad. Sci. U.S.A.* 101 (42):15172-15177), it was sought to determine whether canine soft tumor sarcomas were genetically similar to those of humans and, as such, would be a suitable comparative model. Therefore, the exome of tumor was sequenced and matched to normal DNA from 10 dogs with soft tissue sarcomas (seven peripheral nerve sheath tumors, one fibrosarcoma, one myxosarcoma, and one synovial cell sarcoma) participating in the comparative study (FIG. 10). This analysis involved the interrogation of 30,194 nominal genes comprising 32.9 megabases (Mb) of DNA. On average, 16.2 gigabases (Gb) (range: 8.1-23.3 Gb) of generated sequence were mapped to the genome, and 92.2% of bases in the targeted regions were covered by at least 10 unique reads in the tumor DNA. Similarly, an average of 16.2 Gb (range: 14.6-19.7 Gb) of sequence were mapped to the genome in normal DNA, with 93.6% of targeted bases covered by at least ten unique reads. Average coverage for each targeted base in the tumor was 158-fold (range: 73-227-fold) and 151-fold in the matched normal samples (range: 130-178-fold).

Using stringent analysis criteria, 156 somatic mutations and 28 somatic copy number alterations among the 10 soft tissue sarcomas were identified (FIG. 11 and Table 5). The range of somatic mutations was 0 to 95 with a mean of 16 per tumor. Mutation prevalence in the soft tissue sarcomas was low, averaging 0.47 per Mb (range: 0.00-2.89 per Mb). Excluding one sample outlier, with 95 somatic alterations, there was a mean prevalence of 0.21 mutations per Mb (range: 0.00-0.61 per Mb) (FIG. 10), similar to estimates of the mutation rate in human pediatric rhabdoid tumors (Lee et al. (2012) *J. Clin. Invest.* 122:2983-2988) and other soft tissue sarcomas (Joseph et al. (2014) *Gene Chromosome Canc.* 53:15-24). The most common type of somatic alteration was a missense mutation, with a preponderance of C to T (45.5%) and G to A transitions (34.0%; Tables 6 and 7). Amplifications and deletions were less common, with an average of three per tumor (range: of 0-17) (FIG. 10). Seven of the 10 canine soft tissue sarcomas harbored no amplifications or deletions.

Single base substitutions were identified in three tumor suppressor genes that are frequently mutated in human tumors (NF1, MLL3, and PTCH1). Additionally, MDM4, an oncogene that has been shown to be amplified but not point-mutated in human cancers was found to be amplified (but not point-mutated) in one canine tumor (Lee et al. (2012) *J. Clin. Invest.* 122:2983-2988; Barretina et al. (2010) *Nat. Genet.* 42:715-721; Chmielecki et al. (2013) *Nat. Genet.* 45:131-132; Vogelstein et al. (2013) *Science* 339:1546-1558). The only genes mutated in more than one tumor were ATP7B (missense mutations in two tumors) and AIG1 (amplified in two tumors). Interestingly, mutations in ATP7B were also found in a human liposarcoma (Joseph et al. (2014) *Gene Chromosome Canc.* 53:15-24). Twenty-two of the 184 somatic alterations in canine tumors occurred in genes previously shown to be mutated in human soft tissue sarcomas (Table 8). As the analyses encompassed a number of soft tissue sarcoma histiotypes, larger studies of soft tissue sarcomas in both species will be required to determine whether these represent driver mutations that signify important, conserved tumorigenic pathways. Regardless, the genetic landscapes of canine tumors were similar to those of humans in terms of the numbers of genetic alterations and spectrum of mutations. Specifically, they exclude the possibility that the canine tumors have a very large number of mutations which might make them more likely to mount an immune response than analogous tumor types in humans.

Intratumoral Injection of *C. novyi*-NT Spores in Spontaneous Canine Tumors:

To investigate the safety and efficacy of intratumoral injection of *C. novyi*-NT spores, a comparative study in 16 dogs was performed with spontaneously occurring solid tumors (Table 9). Each dog received at least one cycle of *C. novyi*-NT spore treatment, defined as a single intratumoral injection of 1×10$^8$ *C. novyi*-NT spores into one target tumor. Dogs received up to four cycles of treatment with a one-week interval between cycles. Treated dogs were followed for at least 90 days after the first intratumoral injection.

Nine neutered males, six neutered females and one intact male were enrolled in the study (Table 2). The mean weight of dogs was 29.4 kg (range 8.1-44.3 kg) and their mean age was 10.9 years (range: 7.2-14.3 years). Thirteen dogs had a histomorphic diagnosis of soft tissue sarcoma (eight peripheral nerve sheath tumors, one fibrosarcoma, one myxosarcoma, one rhabdomyosarcoma, and one synovial cell sarcoma), and one each had a diagnosis of osteosarcoma, malignant melanoma, and mast cell tumor. Of the 13 soft tissue sarcomas, six peripheral nerve sheath tumors were available for immunohistochemistry (IHC). All six were positive for S100 and negative for smooth muscle actin, confirming the histiomorphic diagnosis. Seven of the tumors were grade I, five were grade II, and four were grade III. Eight dogs had previous surgical therapy for their cancers.

All dogs received at least one cycle of treatment, with 53 cycles given of a maximum of 64 planned. The majority of dogs, 10 of 16, received the intended four cycles. For dogs showing early tumor responses, toxicity, or progressive disease after the first cycle, subsequent cycles were stopped (Table 9). In general, adverse events were mild in severity (>90% grade I or grade II) and were consistent with local infection at the *C. novyi*-NT spore injection site, including: fever (17 incidents), tumor inflammation (12 incidents), tumor abscess (10 incidents), anorexia (nine incidents), and lethargy (six incidents) (Table 10). Clinical signs of an inflammatory response at the injected target lesion site were observed in 14 of 16 dogs (87.5%), including tumor inflammation (12/14), tumor abscess (7/14), tumor pain (5/14), and tumor discharge (4/14) (Table 11).

Dogs were evaluated for best response on or after day 21 of the study. Two of 16 dogs, 04-R04 and 04-R08, could not be evaluated for responses because the injected tumors were surgically resected before day 21. Dog 04-R04 had a humeral osteosarcoma that experienced robust germination two days after the first intratumoral injection of *C. novyi*-NT and, due to the deep location of the tumor, amputation was performed on day 21 for abscess management. Dog 04-R08 had a peripheral nerve sheath tumor of the medial aspect of the hind paw and received three cycles of treatment before amputation on day 15 for management of progressive disease. Fourteen of 16 dogs were evaluated for responses to treatment. Three had a complete response (CR) to therapy, three had partial responses (PR), five had stable disease (SD), and three had progressive disease (PD). The objective response rate for treatment was 37.5% (6 of 16 dogs; 95 percent confidence interval: 15.2-64.6%). Tumor abscesses and responses occurred after one to four cycles of treatment. Dog 11-R01 experienced a PR after a single cycle, 04-R03 had a CR after three cycles, dogs 04-R02 and 04-R05 had PRs after four cycles, while 04-R01 and 04-R06 had CRs after four cycles. FIG. 5 and FIG. 6 show representative changes in dogs with partial (11-R01) and complete responses (04-R03), respectively. Resolution of abscesses occurred with surgical management in 3 of 6 dogs experiencing an objective response. In these cases, debridement occurred an average of 22 days after the first cycle of treatment. In dog 04-R02, tumor response was assessed before an owner elected amputation for wound management. In dogs 04-R03 and 11-R02 tumor response was assessed after wound debridement. Debrided tissue was available for histopathological analysis in dogs 04-R02 and 04-R03, which demonstrated extensive necrosis and inflammation of the tumor, with numerous gram positive bacilli morphologically consistent with *Clostridium* spp. In dog 04-R02, no viable tumor cells were present at the tumor margin. In dog 04-R03, rare scattered tumor cells were observed. However, given the active nature of *C. novyi*-NT related abscess formation and subsequent immune infiltration and wound healing, it is difficult to speculate on their eventual fate if debridement had not occurred. Regardless of debridement, wound healing was uneventful and complete after 2 to 4 weeks. In addition to surgical management, 3 of 6 dogs that had an objective response received antibiotics (ampicillin, amoxicillin, and metronidazole) and analgesics (opioids, tramadol, and non-steroidal anti-inflammatory drugs) during the course of the study. Overt abscess formation, however, was not always observed before an objective response. Dogs 04-R01 and 04-R06 received 4 cycles of treatment, with tumor inflammation, but not abscess formation, observed at the day 21 study visit. Complete responses were noted on day 42 (unscheduled visit) and day 60 study visits in these two dogs, respectively. Three of the six dogs that experienced either CR or PR had a long-term response (FIG. 7). In the remaining three dogs, mean time to progression was 106 days (range: 60-169).

C. novyi-NT Causes Rapid Local Tumor Destruction in the First Human Patient:

The promising outcomes and favorable risk/benefit profile of C. novyi-NT treatment in the comparative canine trial, in conjunction with the results observed in rats, provided a rationale for attempting this treatment in humans. Accordingly, a Phase I investigational study in human patients with solid tumors that were either refractory to standard therapy or without an available standard therapy was initiated (NCT01924689). The first patient enrolled in this trial is reported herein: a 53-year-old female diagnosed with a retroperitoneal leiomyosarcoma in August 2006. The patient had undergone several surgical resections and received multiple chemotherapy and radiotherapy treatments. However, her disease progressed, with metastatic lesions present in her liver, lungs, peritoneum, and soft tissue in the right shoulder and adjacent right humerus.

Figure 8A:
Figure 8B:
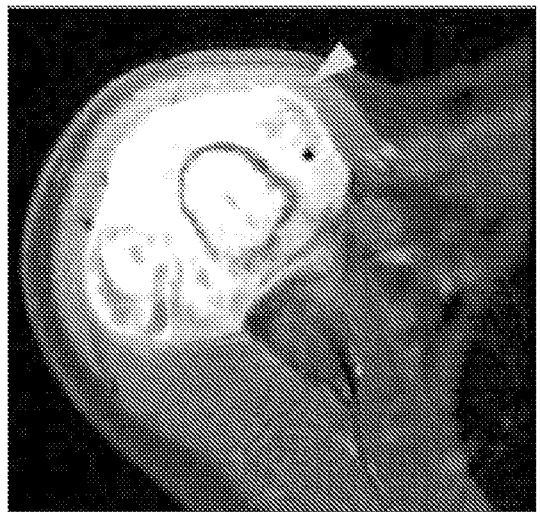
Figure 8C:
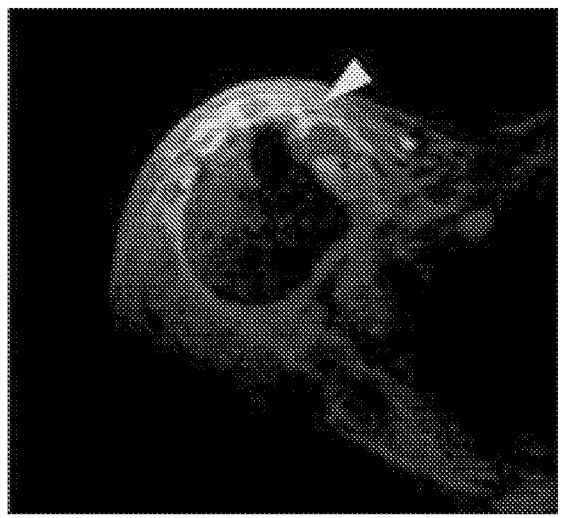
Figure 8D:
Figure 9A:
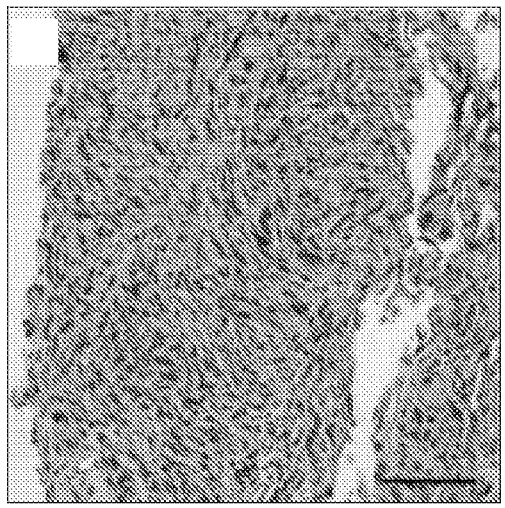
Figure 9B:
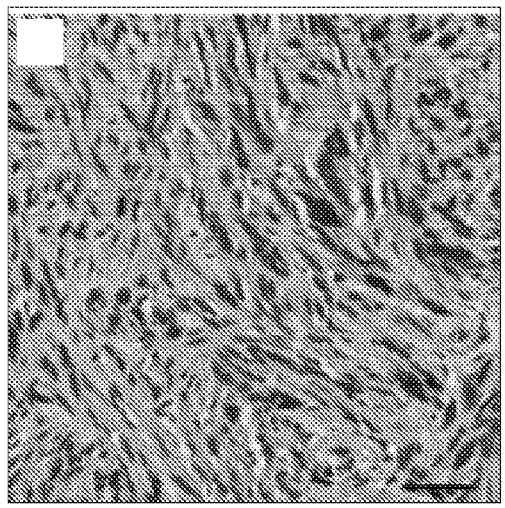
Figure 9C:
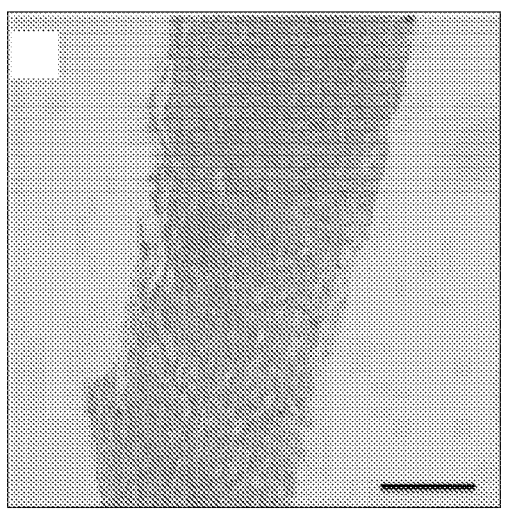
Figure 9D:
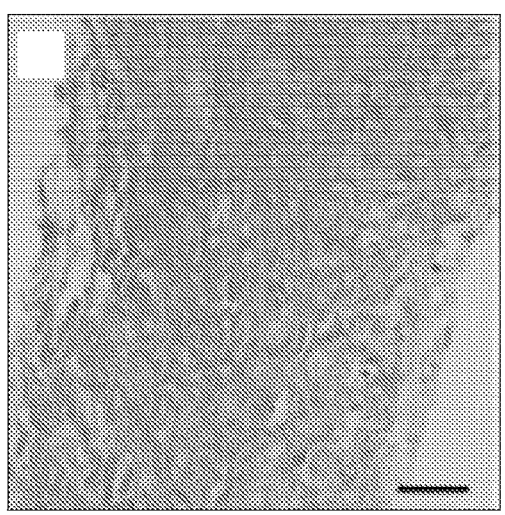

Treatment was performed with the planned starting dose of $1 \times 10^4$ C. novyi-NT spores injected into the patient's metastatic right shoulder tumor with an 18-gauge multi-pronged needle (day 0). On day 1, the patient experienced mild right shoulder pain extending to the scapula, which responded to tramadol and acetaminophen. On day 2, her pain required intravenous patient controlled analgesia with hydromorphone, her leukocyte count increased to 18,300 per µL, and she developed fever with a maximum temperature of 39.2° C. On day 3, the pain in the patient's right shoulder and scapula was difficult to control. Her maximum temperature was 37.8° C. The CT scan of the right upper extremity demonstrated extensive tumor destruction with gas in the soft tissue and bony component of the tumor (FIG. 8A). The permeative pattern of gas was consistent with extensive necrosis of the proximal humerus. A CT-guided aspirate of her tumor revealed C. novyi-NT growth under anaerobic culture conditions. The patient was then started on antibiotics (piperacillin/tazobactam, metronidazole, and vancomycin) and her fever abated shortly thereafter. On day 4, magnetic resonance imaging (MRI) of the right upper extremity demonstrated markedly diminished enhancement confined to the tumor mass compared to baseline (FIGS. 8B and 8C). Biopsies from the tumor showed many gram-positive bacteria and an absence of viable tumor cells (FIG. 9). At the time of the biopsies, a percutaneous drain was placed within the tumor abscess to drain fluid and debris. The patient remained afebrile and her leukocyte count gradually normalized. She continued on antibiotics and was kept in the hospital for intravenous analgesia until day 20 when she was transitioned to oral analgesics. She was discharged on orally administered metronidazole and doxycycline per protocol. On day 29, a follow-up MRI demonstrated an ongoing reduction in tumor enhancement (FIG. 8D). On day 55 the patient presented with localized pain as a result of a patient-effort induced pathological fracture of the necrotic right proximal humerus. Subsequent partial resection of the humerus, debridement, and internal fixation with an intramedullary nail and cement spacer resulted in significant improvement in pain and an increase in range of motion. Intraoperative cultures revealed C. novyi-NT growth under anaerobic culture conditions. Histopathology demonstrated extensive tumor necrosis with small foci of residual tumor cells. The patient continues to be monitored and currently has a performance status of 1 on the Eastern Cooperative Oncology Group scale (ECOG) with no clinical signs of infection.

Discussion

Most conventional anti-cancer therapies target the well-vascularized component of tumors. Yet to cure the disease, every neoplastic cell must be destroyed; any remaining cancer cells can regenerate the tumor. This principle has been dramatically illustrated in recent studies with targeted anti-cancer agents. Though striking remissions can be induced, the tumors nearly always recur within several months due to a tiny fraction (<0.0001%) of cells that harbor resistance mutations prior to therapy (Sharma et al. (2007) Nat. Rev. Cancer 7:169-181; Chapman et al. (2011) New Engl. J. Med 364:2507-2516; Kwak et al. (2010) New Engl. J. Med 363:1693-1703).

Treatment with intratumorally injected C. novyi-NT spores, in principle, offers a way to eradicate neoplastic cells with precision, independent of tumor-specific genetic alterations. In addition to directly killing tumor cells in their hypoxic environments, C. novyi-NT has been shown to induce a potent anti-tumor immune response, both innate and acquired, in pre-clinical models (Agrawal et al. (2004) Proc. Natl. Acad. Sci. U.S.A. 101(42):15172-15177). Although there was no clear evidence to demonstrate an acquired anti-tumor immune response in the human patient or companion dogs, the striking inflammatory response that was induced by intratumoral injection of C. novyi-NT spores provides unequivocal evidence of an innate immune response. As C. novyi-NT is exquisitely sensitive to oxygen and has never been shown to germinate in normoxic areas of tumors, it is plausible that immunity (either innate or acquired) played a role in those dogs in which durable complete responses were obtained. Furthermore, the first human experience with intratumorally injected C. novyi-NT spores resulted in a rapid and robust local anti-tumor response. In this case, proximity of underlying bone may have contributed to a pathological fracture that ultimately required surgery. Patient selection, however, may minimize the risk of similar complications in the future. It is important to point out that this result was produced by only 10,000 spores—a small fraction of the dose used to treat dogs or rats. As the Phase I trial progresses, it will be interesting to see whether higher doses affect distant metastases, either directly through the spread of spores released from the local site into the circulation, or through host-mediated immunity.

Comparative studies in dogs with spontaneous tumors should be incorporated into the debate about the translatability of studies in experimental animal models of cancer (Vail and MacEwen (2000) Cancer Invest. 18:781-792). The demonstration of therapeutic effects in spontaneous tumors of dogs can powerfully complement studies of transplanted or genetically-induced tumors in preclinical animal models. This complementarity is reinforced by the genetic similarities between human and canine tumors described herein. Together, they can provide a compelling rationale for guiding studies in humans, which is particularly germane for new forms of therapy associated with significant potential toxicity, such as those with C. novyi-NT and other biological agents.

The next steps in this line of research are clear. First, it will be important to further characterize the safety and efficacy of intratumoral C. novyi-NT spore treatment. The effects of C. novyi-NT spores, at least when administered systemically, are dramatically enhanced by combination with carefully-chosen chemotherapeutic agents or radiation therapy (Dang et al. (2004) Cancer Bio. Ther. 3:326-337; Cheong et al. (2006) Science 314(5803):1308-1311; Bettegowda et al. (2003) Proc. Natl. Acad. Sci. U.S.A. 100(25): 15083-15088). As the mechanisms through which C. novyi-NT kills tumor cells do not overlap with the mechanisms of action of other forms of therapy, multi-model approaches seem particularly attractive (Dang et al. (2004) Cancer Bio. Ther. 3:326-337). Finally, it will also be of great interest to determine whether immune checkpoint blockade can enhance the anti-tumor immunity expected from intratumoral C. novyi-NT spore treatment (Agrawal et al. (2004) Proc. Natl. Acad. Sci. U.S.A. 101(42):15172-15177).

In some embodiments, the presently disclosed subject matter uses an attenuated strain of the anaerobic, spore-forming bacterium Clostridium novyi (C. novyi-NT) and demonstrates precise, robust, and reproducible anti-tumor responses when C. novyi-NT spores are injected into tumors of rats, pet dogs, and man. These results show that intratumoral C. novyi-NT spores can be used as a therapeutic for patients with locally advanced, non-resectable cancers.

TABLE 1

Performance status evaluations

| Score | Description |
|---|---|
| 0 | Normal activity |
| 1 | Restricted activity: decreased activity from pre-disease status |
| 2 | Compromised: ambulatory only for vital activities, able to consistently defecate and urinate in acceptable areas |
| 3 | Disabled: must be force fed and/or unable to confine urination and defecation to acceptable areas |
| 4 | Death |

TABLE 2

Summary of study evaluations

| | Pretreatment Screening [a] | Day 0[b] | Day 4 | Day 7[b] | Day 11 | Day 14[b] | Day 18 | Day 21[b] | Day 25 | Day 60 | Day 90 |
|---|---|---|---|---|---|---|---|---|---|---|---|
| Informed Consent | X | | | | | | | | | | |
| Medical History & Demographics | X | | | | | | | | | | |
| Physical Exam | X | X | X | X | X | X | X | X | X | X | X |
| Weight & Vital Signs | X | X | X | X | X | X | X | X | X | X | X |
| Performance Score | X | | | | | | | | | | |
| Inclusion & Exclusion Criteria | X | | | | | | | | | | |
| Laboratory Values[c] | X | X | X | X | (X) | (X) | (X) | (X) | (X) | (X) | (X) |
| Imaging [d] | X | (X) | (X) | (X) | (X) | (X) | (X) | (X) | (X) | (X) | (X) |
| Biopsy | X | | | | | | | | | | |
| Research Bloodwork | X | | | | | | | | | | |
| Tumor Measurements and Photographs | X | X | | X | | X | | X | | X | X |
| Intratumoral C. novyi-NT | | X | | X | | X | | X | | X | X |
| Intravenous Fluid Therapy[e] | | X | | X | | X | | X | | | |
| Subcutaneous Fluid Therapy[f] | | | X | | X | | X | | X | | |

[a] Screening evaluations undertaken 1-14 days prior to treatment.
[b] Patient monitored 6 hours post-treatment. Evaluation made every 15 minutes for $1^{st}$ hour post-treatment, every 30 minutes for $2^{nd}$ hour post treatment and every 60 minutes for $3^{rd}$-$6^{th}$ hour post-treatment,
[c] Laboratory values include: complete blood count, serum biochemistry panel, prothrombin time, thromboplastin timem and urinalysis. (X)—at discretion of the investigator.
[d] Diagnostic imaging including: radiographs, ultrasound examination, or computed tomography.
[e] Crystalloid at 4 ml/kg/hr for two hours.
[f] Crystalloid at 20 mL/kg.

TABLE 3

Coded terms to describe tumor adverse events associated with *C. novyi*-NT activity

| System Organ Class (SOC) Term | High Level Term (HLT) | Preferred Term (PT) | Low Level Term (LLT) |
|---|---|---|---|
| Target lesion reaction | Tumor inflammation | Tumor abscess | Tumor abscess |
| Target lesion reaction | Tumor inflammation | Tumor abscess | Tumor closed wound |
| Target lesion reaction | Tumor inflammation | Tumor abscess | Tumor malodorous |
| Target lesion reaction | Tumor inflammation | Tumor abscess | Tumor necrosis |
| Target lesion reaction | Tumor inflammation | Tumor abscess | Tumor open wound |
| Target lesion reaction | Tumor inflammation | Tumor abscess | Tumor tissue loss |
| Target lesion reaction | Tumor inflammation | Tumor abscess | Tumor tissue sloughing |
| Target lesion reaction | Tumor inflammation | Tumor abscess | Tumor ulceration |
| Target lesion reaction | Tumor inflammation | Tumor consistency change | Tumor consistency change |
| Target lesion reaction | Tumor inflammation | Tumor consistency change | Tumor firmer |
| Target lesion reaction | Tumor inflammation | Tumor consistency change | Tumor softer |
| Target lesion reaction | Tumor inflammation | Tumor discharge | Tumor bleeding |
| Target lesion reaction | Tumor inflammation | Tumor discharge | Tumor bloody discharge |
| Target lesion reaction | Tumor inflammation | Tumor discharge | Tumor discharge |
| Target lesion reaction | Tumor inflammation | Tumor discharge | Tumor purulent discharge |
| Target lesion reaction | Tumor inflammation | Tumor discharge | Tumor serious discharge |
| Target lesion reaction | Tumor inflammation | Tumor inflammation | Increased tumor heat |
| Target lesion reaction | Tumor inflammation | Tumor inflammation | Increased tumor warmth |
| Target lesion reaction | Tumor inflammation | Tumor inflammation | Tumor edematous |
| Target lesion reaction | Tumor inflammation | Tumor inflammation | Tumor inflammation |
| Target lesion reaction | Tumor inflammation | Tumor inflammation | Tumor inflammatory reaction |
| Target lesion reaction | Tumor inflammation | Tumor inflammation | Tumor pruritis |
| Target lesion reaction | Tumor inflammation | Tumor inflammation | Tumor swollen |
| Target lesion reaction | Tumor inflammation | Tumor pain | Tumor pain |
| Target lesion reaction | Tumor inflammation | Tumor skin disorder | Tumor bruising |
| Target lesion reaction | Tumor inflammation | Tumor skin disorder | Tumor discoloration |
| Target lesion reaction | Tumor inflammation | Tumor skin disorder | Tumor erythema |
| Target lesion reaction | Tumor inflammation | Tumor skin disorder | Tumor petichiation |
| Target lesion reaction | Tumor inflammation | Other tumor disorder | Other tumor disorder |
| Target lesion reaction | Tumor inflammation | Tumor pain | Tumor discomfort |

TABLE 4

Signs not attributable in VeDDRA to underlying clinical entity or *C. novyi*-NT related target lesion reaction

| Adverse Event (Preferred Term) | G-I | G-II | G-III | G-IV | Number of dogs (with at least 1 occurrence of AE) | Total |
|---|---|---|---|---|---|---|
| Uncoded sign | 15 | 2 | | 1[a] | 5 | 18 |

[a] Grade IV decrease in blood eosinophils reported by investigator.

TABLE 5

Copy number alterations in canine sarcomas[a]

| Case ID | Tumor Type | Gene Symbol | Gene Description | Gene Accession | Nucleotide Position (Genomic) | Fold Amplification |
|---|---|---|---|---|---|---|
| 01-RO2 | STS - PNST | A1G1 | androgen-induced 1 | ENSCAFG00000000303 | chr1: 37686977-37687647 | 5.7 |
| | | XM 844172.1 | uncharacterized protein | ENSCAFG00000023337 | chr2: 7738782-7751246 | 5.9 |
| | | Novel gene | uncharacterized protein | ENSCAFG00000024028 | chr3: 40494283-40494577 | 6.4 |
| | | SIX3 | SIX homeobox 3 | ENSCAFG00000002547 | chr10: 50465860-50469140 | 5.3 |
| | | LST1 | leukocyte specific transcript 1 | ENSCAFG00000023691 | chr12: 4088376-4089275 | 6.7 |
| | | FAM84A | family with sequence similarity 84, member A | ENSCAFG00000003647 | chr17: 13630517-13631423 | 5.0 |

TABLE 5-continued

Copy number alterations in canine sarcomas[a]

| Case ID | Tumor Type | Gene Symbol | Gene Description | Gene Accession | Nucleotide Position (Genomic) | Fold Amplification |
|---|---|---|---|---|---|---|
| | | TLX2 | T-cell leukemia homeobox 2 | ENSCAFG00000008445 | chr17: 51694813-51696234 | 5.1 |
| | | SOX3 | SRY (sex determining region Y)-box 3 | ENSCAFG00000019026 | chrX: 113431902-113433234 | 5.6 |
| | | Novel gene | uncharacterized protein | ENSCAFG00000019588 | chrX: 125230197-125231662 | 5.3 |
| 04-R03 | STS-PNST | A1G1 | androgen-induced 1 | ENSCAFG00000000303 | chr1: 37686977-37687647 | 3.2 |
| | | NKAIN1 | Na+/K+ transporting ATPase interacting 1 | ENSCAFG00000011175 | chr2: 72699008-72705959 | 3.1 |
| 11_R02 | STS-PNST | PIK3C2B | phosphatidyl-inositol-4-phosphate 3-kinase, catalytic subunit type 2 beta | ENSCAFG00000009661 | chr38: 4011051-4013432 | 10.2 |
| | | MDM4 | Mdm4 p53 binding protein homolog | ENSCAFG00000009669 | chr38: 4055972-4103319 | 12.3 |
| | | LRRN2 | leucine rich repeat neuronal 2 | ENSCAFG00000009675 | chr38: 4164479-4166666 | 4.1 |
| | | NFASC | neurofascin | ENSCAFG00000009901 | chr38: 4474563-4542491 | 9.2 |
| | | CNTN2 | contactin 2 (axonal) | ENSCAFG00000024609 | chr38: 4576761-4596329 | 7.3 |
| | | TMEM81 | transmembrane protein 81 | ENSCAFG00000009956 | chr38: 4604335-4605118 | 10.0 |
| | | RBBP5 | retinoblastoma binding protein 5 | ENSCAFG00000009970 | chr38: 4608590-4634589 | 11.4 |
| | | DUSTY CANFA | dual serine/threonine and tyrosine protein kinase | ENSCAFG00000009999 | chr38: 4669577-4715897 | 11.3 |
| | | TMCC2 | transmembrane and coiled-coil domain family 2 | ENSCAFG00000010030 | chr38: 4734043-4773669 | 5.8 |
| | | NUAK2 | NUAK family, SNF1-like kinase, 2 | ENSCAFG00000010038 | chr38: 4798849-4816487 | 7.6 |
| | | KLHDC8A | kelch domain containing 8A | ENSCAFG00000010046 | chr38: 4833445-4838972 | 6.7 |
| | | LEMD1 | LEM domain containing 1 | ENSCAFG00000025208 | chr38: 4872059-4896801 | 10.4 |
| | | CDK18 | cyclin-dependent kinase 18 | ENSCAFG00000010082 | chr38: 4993764-5001820 | 7.7 |
| | | Novel Gene | uncharacterized protein | ENSCAFG00000010109 | chr38: 5028755-5029725 | 6.2 |
| | | MFSD4 | major facilitator superfamily domain containing 4 | ENSCAFG00000010137 | chr38: 5037069-5063455 | 7.6 |
| | | ELK4 | ELK4, ETS-domain protein (SRF accessory protein 1) | ENSCAFG00000010144 | chr38: 5077862-5083778 | 11.7 |
| | | SLC45A3 | solute carrier family 45, member 3 | ENSCAFG00000010148 | chr38: 5111404-5116718 | 5.8 |

[a]Mutation type is amplification

TABLE 6

Types of somatic changes observed across canine soft tissue sarcomas

| Type | Subtype | Number of alterations | Percentage of alterations (%) |
|---|---|---|---|
| Substitutions | Nonsense | 11 | 6 |
| | Missense (non-synonymous) | 135 | 73 |
| | Splice site acceptor | 1 | 1 |
| | Splice site donor | 4 | 2 |
| | Subtotal | 151 | 82 |
| INDELs | Deletion | 4 | 2 |
| | Insertion | 1 | 1 |
| | Subtotal | 5 | 3 |
| CNAs | Deletion | 0 | 0 |
| | Amplification | 28 | 15 |
| | Subtotal | 28 | 15 |
| | Total | 184 | 100 |

INDELs—insertions and deletions: CNAs—copy number alterations.

TABLE 7

Type of somatic mutations across canine soft tissue sarcomas

| Type of somatic alteration | Number | Percentage |
|---|---|---|
| 1 bp deletion | 3 | 1.9 |
| 3bp deletion | 1 | 0.6 |
| 1 bp insertion | 1 | 0.6 |
| A:T > C:G | 3 | 1.9 |
| A:T > G:C | 4 | 2.6 |
| A:T > T:A | 3 | 1.9 |
| C:G > A:T | 4 | 2.6 |
| C:G > G:C | 2 | 1.3 |
| C:G > T:A | 71 | 45.5 |
| G:C > A:T | 53 | 34.0 |
| G:C > C:G | 3 | 1.9 |
| G:C > T:A | 4 | 2.6 |
| T:A > A:T | 1 | 0.6 |
| T:A > C:G | 1 | 0.6 |
| T:A > G:C | 2 | 1.3 |
| Total | 156 | 100 |

TABLE 8

Genes mutated in both human and canine cancers

| Gene | Number of somatic alterations | Type of alteration | Number of samples | Human driver gene or mutated in human soft tissue sarcoma (reference) |
|---|---|---|---|---|
| ANKRD11 | 1 | SBS (splice site) | 1 | (26) |
| ATP7B | 2 | SBS (missense) | 2 | (26) |
| BRDT | 1 | SBS (missense) | 1 | (28) |
| BRWD3 | 1 | SBS (missense) | 1 | (26) |
| CSMD2 | 1 | SBS (missense) | 1 | (26) |
| FCRLB | 1 | SBS (missense) | 1 | (25) |
| IRS1 | 1 | SBS (missense) | 1 | (27) |
| LIMK1 | 1 | SBS (missense) | 1 | (25) |
| MBD5 | 1 | SBS (missense) | 1 | (25) |
| MLL3 | 1 | Deletion | 1 | (29) |
| NF1 | 1 | SBS (missense) | 1 | (27) |
| PKHD1 | 1 | SBS (missense) | 1 | (25) |
| PTCH1 | 1 | SBS (missense) | 1 | (29) |
| PTPRZ1 | 1 | SBS (missense) | 1 | (28) |
| RP1 | 1 | SBS (missense) | 1 | (28) |
| TTN | 4 | SBS (missense) | 1 | (28) |
| MDM4 | 1 | Amplification | 1 | (29) |
| CNTN2 | 1 | Amplification | 1 | (28) |

TABLE 9

Characteristics of the dogs in the comparative canine study

| Case ID | Sex[a] | Breed | Age (years) | Body Weight (kg) | Tumor Type[b] | Grade[c] | Location | Longest Diameter[d] (mm) | Previous Treatment[e] | Number of C. novyi-NT treatment cycles[f] |
|---|---|---|---|---|---|---|---|---|---|---|
| 01-R02 | FN | Border Collie | 14.3 | 21.7 | STS - PNST | II | Left flank | 43 | None | 4 |
| 04-R01 | MN | Golden Retriever | 7.9 | 34.0 | STS - PNST | II | Right maxilla | 15 | Surgical | 4 |
| 04-R02 | MI | Golden Retriever | 12.0 | 38.8 | STS - PNST | I | Right lateral metacarpus | 46 | Surgical | 4 |
| 04-R03 | MN | Boxer | 9.6 | 29.4 | STS - PNST | I | Left medial antebrachium | 56 | None | 3[TR] |
| 04-R04 | FN | St. Bernard | 11.7 | 31.0 | OSA$_c$ | III | Right proximal humerus | ND | Surgical | 1[AE] |
| 04-R05 | MN | Shetland Sheepdog | 14.0 | 13.4 | STS - RMS | III | Right cranial antebrachium | 45 | Surgical & C. novyi-NT spores IV | 4 |
| 04-R06 | FN | Labrador Retriever | 11.6 | 24.3 | MCT | III | Right hindlimb digit III | 23 | None | 4 |
| 04-R08 | FN | Shepherd | 7.2 | 28.9 | STS - PNST | I | Right medial hindlimb paw | 65 | Surgical | 3[PD] |
| 10-R01 | MN | Golden Retriever | 13.7 | 33.6 | OMM | III | Left mandible | 27 | Surgical | 2[AE] |
| 10-R02 | MN | Pit Bull Terrier | 10.0 | 43.6 | STS - PNST | I | Right flank | 53 | Surgical | 4 |
| 11-R01 | MN | Maltese | 11.1 | 8.1 | STS - PNST | II | Left pinna | 28 | Surgical | 1[TR] |
| 11-R02 | FN | Labrador Retriever | 12.2 | 30.3 | STS - PNST | II | Left stifle | 43 | None | 3[IV] |
| 11-R04 | MN | Husky | 10.3 | 44.3 | STS - FBS | I | Right forelimb paw | 29 | None | 4 |
| 16-R02 | MN | Labrador Retriever | 9.8 | 36.8 | STS - MXS | I | Left lateral thigh | 91 | Surgical | 4 |
| 16-R03 | FN | Shepherd | 10.8 | 20.8 | STS - SCS | I | Left forelimb paw | 53 | Surgical | 4 |
| 26-R01 | MN | Labrador Retriever | 7.9 | 30.8 | STS - RMS | II | Right forelimb paw | 24 | None | 4 |

[a]FN—female neutered; MN—male neutered; MI—male intact.
[b]STS—soft tissue sarcoma; STS - PNST—peripheral nerve sheath tumor; OSAc—chondroblastic osteosarcoma; STS - RMS—rhabdomyosarcoma; MCT—mast cell tumor; OMM—oral malignant melamona; STS - FBS—fibrosarcoma; STS - MXS—myxosarcoma; STS—synovial cell sarcoma.
[c]Grading based on published criteria (42-45): I—low grade; II—intermediate grade; III—high grade; NA—not assessed.
[d]longest diameter at time of first C. novyi-NT injection (day 0). ND—immeasurable due to location.
[e]04-R05—previous C. novyi-NT therapy with a single intravenous injection of 1 × 10$^7$ spores/m$^2$ 437 days prior to the first intratumoral injection of C. novyi-NT spores.
[f]A treatment cycle consisted of one intratumoral injection of 1 × 10$^8$ C. novyi-NT spores. Dogs received up to 4 cycles, typically 1 week apart. Reason for receiving fewer than four treatment cycles given in superscript: TR—tumor response; AE—adverse event; PD—progressive disease; IV—4$^{th}$ dose given intravenously.

TABLE 10

Summary of adverse events observed throughout study

| Adverse Event (Preferred Term) | G-I | G-II | G-III | G-IV | Number of dogs (with at least 1 occurrence of AE) | Total |
|---|---|---|---|---|---|---|
| Hyperthermia | 14 | 3 | | | 10 | 17 |
| Tumor inflammation | 7 | 4 | 1 | | 12 | 12 |
| Tumor abscess | 6 | 3 | 1 | | 8 | 10 |
| Anorexia | 7 | 2 | | | 8 | 9 |
| Lethargy | 3 | 2 | 1 | | 6 | 6 |
| Lameness | 5 | | 1 | | 6 | 6 |
| Oedema | 5 | 1 | | | 5 | 6 |
| Hypertension | 6 | | | | 4 | 6 |
| Neutrophilia | 6 | | | | 6 | 6 |
| Tumor discharge | 6 | | | | 4 | 6 |
| Anaemia | 4 | | 1 | | 5 | 5 |
| Diarrhoea | | 3 | 1 | | 2 | 4 |
| Tumor pain | 3 | 1 | | | 4 | 4 |
| Leucocytosis | 4 | | | | 3 | 4 |
| Lymphadenitis | 4 | | | | 4 | 4 |
| Tumor consistency change | 3 | | | | 3 | 3 |
| Leucopenia | | 1 | | 1 | 1 | 2 |
| Thrombocytopenia | 1 | | | 1 | 2 | 2 |
| Localized pain | | 1 | 1 | | 2 | 2 |
| Lymphopenia | 1 | | 1 | | 2 | 2 |
| Change in blood protein | 1 | 1 | | | 2 | 2 |
| Emesis | 1 | 1 | | | 2 | 2 |
| Fluid in abdomen | 1 | 1 | | | 1 | 2 |
| General pain | 1 | 1 | | | 2 | 2 |
| Electrolyte disorder | 2 | | | | 2 | 2 |
| Impaired consciousness | 2 | | | | 2 | 2 |
| Tumor skin disorder | 2 | | | | 2 | 2 |
| Neutropenia | | | | 1 | 1 | 1 |
| Malaise | | 1 | | | 1 | 1 |
| Muscle weakness | | | 1 | | 1 | 1 |
| Recumbency | | | 1 | | 1 | 1 |
| Steatitis | | | 1 | | 1 | 1 |
| Digestive tract haemorrhage | | 1 | | | 1 | 1 |
| Skin and tissue infection | | 1 | | | 1 | 1 |
| Arrhythmia | 1 | | | | 1 | 1 |
| Bone and joint disorder | 1 | | | | 1 | 1 |
| Cardiac enlargement | 1 | | | | 1 | 1 |
| Digestive tract disorder | 1 | | | | 1 | 1 |
| Eosinophilia | 1 | | | | 1 | 1 |
| Erythema | 1 | | | | 1 | 1 |
| Hepatomegaly | 1 | | | | 1 | 1 |
| Hepatopathy | 1 | | | | 1 | 1 |
| Injection site pruritus | 1 | | | | 1 | 1 |
| Lymphocytosis | 1 | | | | 1 | 1 |
| Murmur | 1 | | | | 1 | 1 |
| Nausea | 1 | | | | 1 | 1 |
| Palpable mass | 1 | | | | 1 | 1 |
| Pulmonary disorder | 1 | | | | 1 | 1 |
| Skin haemorrhage | 1 | | | | 1 | 1 |
| Urine abnormalities | 1 | | | | 1 | 1 |
| Total | | | | | | 153 |

TABLE 11

Summary of clinical responses to Intratumoral *C. novyi*-NT therapy

| Case ID | Clinical evidence of germination[a] | Clinical Response[b] |
|---|---|---|
| 01-R02 | Tumor inflammation, skin disorder and discharge | PD |
| 04-R01 | Tumor inflammation and pain | CR |
| 04-R02 | Tumor inflammation and abscess | PR |
| 04-R03 | Tumor inflammation, consistency change, discharge and tumor pain | CR |
| 04-R04 | Tumor inflammation and pain | NE PR |
| 04-R05 | Tumor inflammation, consistency change, skin disorder and pain | |
| 04-R06 | Tumor inflammation, abscess and discharge | CR |
| 04-R08 | Tumor abscess and discharge | NE |
| 10-R01 | — | PD |
| 10-R02 | Tumor inflammation, abscess and pain | SD |
| 11-R01 | Tumor inflammation and abscess | PR |
| 11-R02 | Tumor inflammation | SD |
| 11-R04 | Tumor abscess and consistency change | SD |
| 16-R02 | Tumor inflammation | PD |
| 16-R03 | Tumor inflammation and abscess | SD |
| 26-R01 | — | SD |

[a]Clinical evidence of *C. novyi*-NT germination on or after day 0 of the study, includes target lesion reactions (Table 3).
[b]Best response of the target lesion, as defined by the study protocol, after day 21 of the study: CR, complete response; PR, partial response; SD, stable disease; PD, progressive disease; NE, not evaluated for response on or after day 21 of the study.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for debulking a solid colon tumor in a subject, the method comprising administering to the subject a therapeutically effective amount of a combination of an anti-CTLA-4 antibody, and one or more *Clostridium novyi* bacterium spores, wherein no additional anti-cancer agent is administered.

2. The method of claim 1, wherein the *Clostridium novyi* bacterium spores are toxin-depleted and anaerobic.

3. The method of claim 2, wherein the *Clostridium novyi* bacterium spores is *Clostridium novyi*-NT bacterium spores.

4. The method of claim 2, wherein part of or all of a toxin gene of a wild-type form of the *Clostridium novyi* bacterium spores is deleted.

5. The method of claim 2, wherein the toxicity of the *Clostridium novyi* bacterium spores is reduced by a factor of at least 2 compared to a corresponding wild-type *Clostridium novyi* bacterium spores.

6. The method of claim 1, wherein the *Clostridium novyi* bacterium spores are administered intravenously or intratumorally.

7. The method of claim 1, wherein the anti-CTLA-4 antibody is administered by at least one method selected from the group consisting of intravenously, intramuscularly, subcutaneously, and intratumorally.

8. The method of claim 1, wherein the solid colon tumor is malignant.

9. The method of claim 1, wherein the subject is human.

10. The method of claim 1, wherein the subject is a non-human animal.

\* \* \* \* \*